(12) United States Patent
Lau et al.

(10) Patent No.: US 6,517,570 B1
(45) Date of Patent: *Feb. 11, 2003

(54) EXTERIOR SUPPORTED SELF-EXPANDING STENT-GRAFT

(75) Inventors: Lilip Lau, Sunnyvale, CA (US); Charles Maroney, Portola Valley, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/903,210

(22) Filed: Jul. 21, 1997

Related U.S. Application Data

(63) Continuation of application No. 08/740,030, filed on Oct. 23, 1996, now abandoned, which is a continuation of application No. 08/299,190, filed on Aug. 31, 1994, now abandoned.

(51) Int. Cl.$^7$ .................................................. A61F 2/06
(52) U.S. Cl. ..................... 623/1.13; 623/1.22; 623/23.7; 606/195
(58) Field of Search .............................. 623/1, 11, 1.13, 623/1.22, 23.69, 23.7; 606/191, 194, 195, 198

(56) References Cited

U.S. PATENT DOCUMENTS

| | | |
|---|---|---|
| 2,638,093 A | 5/1953 | Kulick |
| 3,029,819 A | 4/1962 | Starks |
| 3,096,560 A | 7/1963 | Liebig |
| 3,142,067 A | 7/1964 | Liebig |
| 3,152,618 A | 10/1964 | Rothermal et al. |
| 3,174,851 A | 3/1965 | Buehur et al. |
| 3,351,463 A | 11/1967 | Rozner et al. |
| 3,479,670 A | 11/1969 | Medell |

(List continued on next page.)

FOREIGN PATENT DOCUMENTS

| | | |
|---|---|---|
| AU | B-42485/89 | 4/1990 |

(List continued on next page.)

OTHER PUBLICATIONS

Laborde et al., "Intraluminal Bypass of Abdominal Aortic Aneurysm: Feasibility Study", *Radiology* 1992, 184:185–190.

MinTec™ Minimally Invasive Technologies Product Brochure for the Craggstent and Cragg EndoPro System 1,4, pages total.

(List continued on next page.)

*Primary Examiner*—Paul B. Prebilic
(74) *Attorney, Agent, or Firm*—Morgan & Finnegan, LLP

(57) ABSTRACT

This is a medical device and a method of using it. The device is a foldable stent-graft which may be percutaneously delivered with (or on) an endovascular catheter, via surgical techniques or using other suitable techniques and then expanded. The stent-graft uses a kink-resistant stent structure and an interior graft which is attached to the stent in such a way that the graft does not kink and yet the stent is able to conform to curves in the blood vessel lumen. The expandable stent structure preferably has a helically deployed torsional member with an undulating shape which is wound to form the generally cylindrical shape deployed as the stent. The helical winding desirably is aligned to allow undulations in adjacent turns of the helix to be in phase. The adjacent undulating shapes are held in that phased relationship using a flexible linkage, typically made of a polymeric material. The graft component cooperating with the stent is tubular and mounted on the interior of the stent. Although it may be made of any variety of materials, it preferably is an expanded polyfluorocarbon. The graft component may be bound to the flexible linkage which holds the stent windings in phase (or the stent structure itself) at a number of sliding attachment points.

23 Claims, 9 Drawing Sheets

U.S. PATENT DOCUMENTS

| | | |
|---|---|---|
| 3,514,791 A | 6/1970 | Sparks |
| 3,562,820 A | 2/1971 | Braun |
| 3,625,198 A | 12/1971 | Sparks |
| 3,657,744 A | 4/1972 | Ersek |
| 3,710,777 A | 1/1973 | Sparks |
| 3,753,700 A | 8/1973 | Harrison et al. |
| 3,774,596 A | 11/1973 | Cook |
| 3,805,301 A | 4/1974 | Liebig |
| 3,866,247 A | 2/1975 | Sparks |
| 3,866,609 A | 2/1975 | Sparks |
| 3,868,956 A | 3/1975 | Alfidi et al. |
| 3,927,422 A | 12/1975 | Sawyer |
| 3,938,524 A | 2/1976 | Sparks |
| 3,949,073 A | 4/1976 | Daniels et al. |
| 3,953,566 A | 4/1976 | Gore |
| 3,974,526 A | 8/1976 | Dardik et al. |
| 3,993,045 A | 11/1976 | Ion |
| 4,011,861 A | 3/1977 | Enger |
| 4,047,252 A | 9/1977 | Liebig et al. |
| 4,130,904 A | 12/1978 | Whalen |
| 4,140,126 A | 2/1979 | Choudhury |
| 4,164,045 A | 8/1979 | Bokros et al. |
| 4,187,390 A | 2/1980 | Gore |
| 4,300,244 A | 11/1981 | Bokros |
| 4,306,318 A | 12/1981 | Mano et al. |
| 4,319,363 A | 3/1982 | Ketharanathan |
| 4,355,426 A | 10/1982 | MacGregor |
| 4,411,655 A | 10/1983 | Schreck |
| 4,424,208 A | 1/1984 | Wallace et al. |
| 4,425,908 A | 1/1984 | Simon |
| 4,488,911 A | 12/1984 | Luck et al. |
| 4,494,531 A | 1/1985 | Gianturco |
| 4,502,159 A | 3/1985 | Woodroof et al. |
| 4,503,569 A | 3/1985 | Dotter |
| 4,512,338 A | 4/1985 | Balko et al. |
| 4,517,687 A | 5/1985 | Liebig et al. |
| 4,530,113 A | 7/1985 | Matterson |
| 4,546,500 A | 10/1985 | Bell |
| 4,553,545 A | 11/1985 | Maass et al. |
| 4,557,764 A | 12/1985 | Chu |
| 4,562,596 A | 1/1986 | Kornberg |
| 4,580,568 A | 4/1986 | Gianturco |
| 4,582,640 A | 4/1986 | Smestad et al. |
| 4,592,754 A | 6/1986 | Gupte et al. |
| 4,604,762 A | 8/1986 | Robinson |
| 4,617,932 A | 10/1986 | Kornberg |
| 4,629,458 A | 12/1986 | Pinchuk |
| 4,641,653 A | 2/1987 | Rockey |
| 4,642,117 A | 2/1987 | Nguyen et al. |
| 4,647,416 A | 3/1987 | Seiler, Jr. et al. |
| 4,649,922 A | 3/1987 | Wiktor |
| 4,655,771 A | 4/1987 | Wallsten |
| 4,665,906 A | 5/1987 | Jervis |
| 4,689,399 A | 8/1987 | Chu |
| 4,728,328 A | 3/1988 | Hughes et al. |
| 4,733,665 A | 3/1988 | Palmaz |
| 4,738,666 A | 4/1988 | Fuqua |
| 4,739,762 A | 4/1988 | Palmaz |
| 4,740,207 A | 4/1988 | Kreamer |
| 4,760,849 A | 8/1988 | Kropf |
| 4,776,337 A | 10/1988 | Palmaz |
| 4,787,899 A | 11/1988 | Lazarus |
| 4,790,313 A | 12/1988 | Borrelly |
| 4,795,458 A | 1/1989 | Regan |
| 4,798,606 A | 1/1989 | Pinchuk |
| 4,800,882 A | 1/1989 | Gianturco |
| 4,816,028 A | 3/1989 | Kapadia et al. |
| 4,816,339 A | 3/1989 | Tu et al. |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,856,516 A | 8/1989 | Hillstead |
| 4,877,025 A | 10/1989 | Hanson |
| 4,878,906 A | 11/1989 | Lindemann et al. |
| 4,886,062 A | 12/1989 | Wiktor |
| 4,886,500 A | 12/1989 | Lazarus |
| 4,892,539 A | 1/1990 | Koch |
| 4,913,141 A | 4/1990 | Hillstead |
| 4,921,479 A | 5/1990 | Grayzel |
| 4,941,870 A | 7/1990 | Okada et al. |
| 4,950,227 A | 8/1990 | Savin et al. |
| 4,955,899 A | 9/1990 | Della Corna et al. |
| 4,957,504 A | 9/1990 | Chardack |
| 4,957,508 A * | 9/1990 | Kaneko et al. ................ 623/1 |
| 4,969,458 A | 11/1990 | Wiktor |
| 4,990,151 A | 2/1991 | Wallsten |
| 4,990,155 A | 2/1991 | Wilkoff |
| 4,994,071 A | 2/1991 | MacGregor |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,042,161 A | 8/1991 | Hodge |
| 5,064,435 A | 11/1991 | Porter |
| 5,066,298 A | 11/1991 | Hess |
| 5,067,957 A | 11/1991 | Jervis |
| 5,078,726 A | 1/1992 | Kreamer |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,424 A | 4/1992 | Hoffman, Jr. et al. |
| 5,122,154 A | 6/1992 | Rhodes |
| 5,123,917 A | 6/1992 | Lee |
| 5,127,919 A | 7/1992 | Ibrahim et al. |
| 5,133,732 A | 7/1992 | Wiktor |
| 5,139,480 A | 8/1992 | Hickle et al. |
| 5,147,370 A | 9/1992 | McNamara et al. |
| 5,151,105 A | 9/1992 | Kwan-Gett |
| 5,156,619 A | 10/1992 | Ehrenfeld |
| 5,161,547 A | 11/1992 | Tower |
| 5,162,430 A | 11/1992 | Rhee et al. |
| 5,163,958 A | 11/1992 | Pinchuk |
| 5,171,262 A | 12/1992 | MacGregor |
| 5,178,630 A | 1/1993 | Schmitt |
| 5,192,289 A | 3/1993 | Jessen |
| 5,192,307 A | 3/1993 | Wall |
| 5,195,984 A | 3/1993 | Schatz |
| 5,197,977 A | 3/1993 | Hoffman, Jr. et al. |
| 5,197,978 A | 3/1993 | Hess |
| 5,201,757 A | 4/1993 | Heyn |
| 5,209,735 A | 5/1993 | Lazarus |
| 5,211,658 A | 5/1993 | Clouse |
| 5,213,580 A | 5/1993 | Slepian et al. |
| 5,217,483 A | 6/1993 | Tower |
| 5,221,261 A | 6/1993 | Termin et al. |
| 5,226,913 A | 7/1993 | Pinchuk |
| 5,232,446 A | 8/1993 | Arney |
| 5,236,447 A | 8/1993 | Kubo et al. |
| 5,242,451 A | 9/1993 | Harada et al. |
| 5,246,452 A | 9/1993 | Sinnott |
| 5,258,042 A | 11/1993 | Mehta |
| 5,264,276 A | 11/1993 | McGregor et al. |
| 5,271,410 A | 12/1993 | Wolzinger et al. |
| 4,733,365 A | 1/1994 | Palmaz |
| 5,276,276 A | 1/1994 | Gunn |

| Patent No. | | Date | Inventor(s) |
|---|---|---|---|
| 5,282,824 A | * | 2/1994 | Gianturco .................... 623/1 |
| 5,282,846 A | | 2/1994 | Schmitt |
| 5,282,847 A | | 2/1994 | Trescony et al. |
| 5,282,848 A | | 2/1994 | Schmitt |
| 5,290,305 A | | 3/1994 | Inoue |
| 5,306,261 A | | 4/1994 | Alliger et al. |
| 5,306,294 A | | 4/1994 | Wnston et al. |
| 5,314,472 A | | 5/1994 | Fontaine |
| 5,324,304 A | | 6/1994 | Ramussen |
| 5,324,323 A | | 6/1994 | Bui |
| 5,330,528 A | | 7/1994 | Lazim |
| 5,336,254 A | | 8/1994 | Brennen et al. |
| 5,342,348 A | | 8/1994 | Kaplan |
| 5,342,387 A | | 8/1994 | Summers |
| 5,344,426 A | | 9/1994 | Lau et al. |
| 5,348,537 A | | 9/1994 | Wiesner et al. |
| 5,354,308 A | | 10/1994 | Simon et al. |
| 5,354,309 A | | 10/1994 | Schnepp-Pesch et al. |
| 5,356,423 A | | 10/1994 | Tihon et al. |
| 5,360,443 A | * | 11/1994 | Barone et al. ................ 623/1 |
| 5,366,472 A | | 11/1994 | Hillstead |
| 5,366,473 A | | 11/1994 | Winston et al. |
| 5,366,504 A | | 11/1994 | Andersen et al. |
| 5,370,691 A | | 12/1994 | Samson |
| 5,372,600 A | | 12/1994 | Beyar |
| 5,382,261 A | | 1/1995 | Palmaz |
| 5,383,928 A | | 1/1995 | Scott et al. |
| 5,385,580 A | | 1/1995 | Schmitt |
| 5,387,235 A | | 2/1995 | Chuter |
| 5,405,377 A | * | 4/1995 | Cragg .................... 606/191 |
| 5,405,378 A | | 4/1995 | Strecker |
| 5,413,598 A | | 5/1995 | Moreland |
| 5,421,955 A | | 6/1995 | Lau et al. |
| 5,423,849 A | | 6/1995 | Eugelson et al. |
| 5,425,710 A | | 6/1995 | Kahir et al. |
| 5,425,739 A | | 6/1995 | Jessen |
| 5,443,500 A | | 8/1995 | Sigwart |
| 5,449,373 A | | 9/1995 | Pinchasik et al. |
| 5,453,084 A | | 9/1995 | Moses |
| 5,456,713 A | | 10/1995 | Chuter |
| 5,456,721 A | | 10/1995 | Legrand |
| 5,458,605 A | | 10/1995 | Klemm |
| 5,458,615 A | | 10/1995 | Klemm et al. |
| 5,464,449 A | | 11/1995 | Ryan et al. |
| 5,476,506 A | | 12/1995 | Lunn |
| 5,480,423 A | | 1/1996 | Ravenscroft et al. |
| 5,484,444 A | | 1/1996 | Braudschweiler |
| 5,487,858 A | | 1/1996 | Schmitt |
| 5,489,295 A | | 2/1996 | Piplani et al. |
| 5,496,364 A | | 3/1996 | Schmitt |
| 5,496,365 A | | 3/1996 | Sgro |
| 5,499,994 A | | 3/1996 | Tihon et al. |
| 5,507,767 A | | 4/1996 | Maeda et al. |
| 5,507,769 A | | 4/1996 | Marin et al. |
| 5,507,771 A | | 4/1996 | Gianturco |
| 5,509,902 A | | 4/1996 | Raulerson |
| 5,509,931 A | | 4/1996 | Schmitt |
| 5,514,154 A | * | 5/1996 | Lau et al. ................ 606/195 |
| 5,522,822 A | | 6/1996 | Phelps et al. |
| 5,522,880 A | | 6/1996 | Barone et al. |
| 5,522,881 A | * | 6/1996 | Lentz .................... 623/11 |
| 5,522,961 A | | 6/1996 | Leonhardt |
| 5,540,701 A | | 7/1996 | Sharkey et al. |
| 5,540,712 A | | 7/1996 | Kleshinski et al. |
| 5,545,210 A | | 8/1996 | Hess et al. |
| 5,545,211 A | | 8/1996 | An et al. |
| 5,549,635 A | | 8/1996 | Solar |
| 5,549,663 A | | 8/1996 | Cottone, Jr. |
| 5,554,180 A | | 9/1996 | Turk |
| 5,554,181 A | | 9/1996 | Das |
| 5,554,182 A | | 9/1996 | Dinh et al. |
| 5,556,413 A | | 9/1996 | Lam |
| 5,562,724 A | | 10/1996 | Vorwerk et al. |
| 5,562,726 A | * | 10/1996 | Chuter .................... 606/194 |
| 5,562,727 A | | 10/1996 | Turk et al. |
| 5,571,166 A | | 11/1996 | Dinh et al. |
| 5,571,169 A | | 11/1996 | Plaia et al. |
| 5,571,172 A | | 11/1996 | Chin |
| 5,571,173 A | | 11/1996 | Parodi |
| 5,571,176 A | | 11/1996 | Taheri |
| 5,575,815 A | | 11/1996 | Slepian et al. |
| 5,575,816 A | | 11/1996 | Rudnick et al. |
| 5,575,817 A | | 11/1996 | Martin |
| 5,578,071 A | | 11/1996 | Parodi |
| 5,591,197 A | | 1/1997 | Orth et al. |
| 5,591,198 A | | 1/1997 | Boyle et al. |
| 5,591,228 A | | 1/1997 | Edoga |
| 5,591,229 A | | 1/1997 | Parodi |
| 5,599,305 A | | 2/1997 | Hermann et al. |
| 5,607,442 A | | 3/1997 | Fischell et al. |
| 5,607,444 A | | 3/1997 | Lam |
| 5,607,445 A | | 3/1997 | Summers |
| 5,609,625 A | | 3/1997 | Piplani et al. |
| 5,609,627 A | | 3/1997 | Goicoechea et al. |
| 5,620,763 A | | 4/1997 | House et al. |
| 5,622,188 A | | 4/1997 | Plaia et al. |
| 5,626,561 A | | 5/1997 | Butler et al. |
| 5,628,783 A | | 5/1997 | Quiachon et al. |
| 5,628,784 A | | 5/1997 | Strecker |
| 5,628,788 A | | 5/1997 | Pinchuk |
| 5,632,763 A | | 5/1997 | Glastra |
| 5,632,772 A | | 5/1997 | Alcime et al. |
| 5,637,113 A | | 6/1997 | Tartaglia et al. |
| 5,639,278 A | | 6/1997 | Dereueme et al. |
| 5,643,208 A | | 7/1997 | Parodi |
| 5,647,380 A | | 7/1997 | Campbell et al. |
| 5,649,978 A | | 7/1997 | Samson |
| 5,653,743 A | | 8/1997 | Martin |
| 5,653,748 A | | 8/1997 | Strecker |
| 5,662,614 A | | 9/1997 | Edoga |
| 5,662,675 A | | 9/1997 | Polanskyj Stockert et al. |
| 5,662,701 A | | 9/1997 | Plaia et al. |
| 5,662,713 A | | 9/1997 | Andersen et al. |
| 5,665,117 A | | 9/1997 | Rhodes |
| 5,667,523 A | | 9/1997 | Bynon et al. |
| 5,669,924 A | | 9/1997 | Shaknovich |
| 5,669,930 A | | 9/1997 | Igarashi |
| 5,674,276 A | | 10/1997 | Andersen et al. |
| 5,676,671 A | | 10/1997 | Inoue |
| 5,676,696 A | | 10/1997 | Marcade |
| 5,676,697 A | | 10/1997 | McDonald |
| 5,681,346 A | | 10/1997 | Orth et al. |
| 5,683,449 A | | 11/1997 | Marcade |
| 5,683,450 A | | 11/1997 | Goicoechea et al. |
| 5,683,451 A | | 11/1997 | Lenker et al. |
| 5,683,452 A | | 11/1997 | Barone et al. |
| 5,693,084 A | | 12/1997 | Chuter |
| 5,693,086 A | | 12/1997 | Goicoechea et al. |
| 5,693,087 A | | 12/1997 | Parodi |
| 5,693,088 A | | 12/1997 | Lazarus |
| 5,695,517 A | | 12/1997 | Marin et al. |
| 5,697,970 A | | 12/1997 | Schmitt et al. |
| 5,700,285 A | | 12/1997 | Myers et al. |
| 5,700,286 A | | 12/1997 | Taraglia |
| 5,709,657 A | | 1/1998 | Zimmon |
| 5,713,917 A | | 2/1998 | Leonhardt et al. |
| 5,716,365 A | | 2/1998 | Goicoechea et al. |
| 5,718,724 A | | 2/1998 | Goicoechea et al. |
| 5,718,973 A | | 2/1998 | Lewis et al. |
| 5,720,776 A | | 2/1998 | Chuter et al. |
| 5,723,003 A | | 3/1998 | Winston et al. |
| 5,723,004 A | | 3/1998 | Dereume et al. |

| | | | |
|---|---|---|---|
| 5,728,131 A | 3/1998 | Frantzen et al. | |
| 5,728,150 A | 3/1998 | McDonald et al. | |
| 5,730,698 A | 3/1998 | Fischell et al. | |
| 5,732,572 A | 3/1998 | Litton | |
| 5,735,892 A | 4/1998 | Meyers et al. | |
| 5,741,274 A | 4/1998 | Lenker et al. | |
| 5,741,325 A | 4/1998 | Chaikof et al. | |
| 5,749,825 A | 5/1998 | Fischell et al. | |
| 5,749,880 A | 5/1998 | Banas et al. | |
| 5,749,921 A | 5/1998 | Lenker et al. | |
| 5,755,769 A | 5/1998 | Richard et al. | |
| 5,769,882 A | 6/1998 | Fogarty et al. | |
| 5,779,732 A | 7/1998 | Amundson | |
| 5,782,904 A * | 7/1998 | White et al. | 623/1 |
| 5,800,521 A | 9/1998 | Orth | |
| 5,800,522 A | 9/1998 | Campbell et al. | |
| 5,800,524 A | 9/1998 | Borghi | |
| 5,810,870 A | 9/1998 | Myers et al. | |
| 5,824,041 A | 10/1998 | Lenker et al. | |
| 5,843,069 A | 12/1998 | Butler et al. | |
| 5,843,171 A | 12/1998 | Campbell et al. | |
| 5,865,723 A | 2/1999 | Love | |
| 5,868,704 A | 2/1999 | Campbell et al. | |
| 5,873,906 A | 2/1999 | Lau et al. | |
| 5,876,432 A | 3/1999 | Lau et al. | |
| 5,888,243 A | 3/1999 | Silvestrini | |
| 5,919,225 A | 7/1999 | Lau et al. | |
| 5,925,061 A | 7/1999 | Ogi et al. | |
| 5,925,075 A | 7/1999 | Myers et al. | |
| 5,935,161 A * | 8/1999 | Robinson et al. | 623/1 |
| 5,961,546 A * | 10/1999 | Robinson et al. | 623/1 |
| 5,972,441 A | 10/1999 | Campbell et al. | |
| 5,976,650 A | 11/1999 | Campbell et al. | |
| 5,993,489 A | 11/1999 | Lewis et al. | |
| 6,001,123 A | 12/1999 | Lau | |
| 6,015,429 A | 1/2000 | Lau et al. | |
| 6,015,431 A | 1/2000 | Thornton et al. | |
| 6,017,362 A | 1/2000 | Lau | |
| 6,019,787 A | 1/2000 | Richard et al. | |
| 6,019,788 A | 1/2000 | Butters et al. | |
| 6,025,044 A | 2/2000 | Campbell et al. | |
| 6,027,779 A | 2/2000 | Campbell et al. | |
| 6,027,811 A | 2/2000 | Campbell et al. | |
| 6,042,605 A | 3/2000 | Martin et al. | |
| 6,048,484 A | 4/2000 | House et al. | |
| 6,086,604 A | 7/2000 | Fischell et al. | |
| 6,120,477 A | 9/2000 | Campbell et al. | |
| 6,139,572 A | 10/2000 | Campbell et al. | |
| 6,159,565 A | 12/2000 | Campbell et al. | |
| 6,165,210 A | 12/2000 | Lau et al. | |
| 6,193,745 B1 | 2/2001 | Fogarty et al. | |
| 6,203,568 B1 | 3/2001 | Lombardi et al. | |

FOREIGN PATENT DOCUMENTS

| | | |
|---|---|---|
| AU | B-34742/93 | 1/1993 |
| CA | 2026604 | 4/1991 |
| CA | 2079417 | 4/1993 |
| DE | 37 24 514 A1 | 2/1989 |
| DE | 39 18736 A1 | 12/1990 |
| DE | 41 37 857 A1 | 5/1992 |
| DE | 196 17 723 A | 11/1997 |
| EP | 0 382 014 | 8/1990 |
| EP | 0 408 245 | 1/1991 |
| EP | 0 418 677 | 3/1991 |
| EP | 0 423 916 B1 | 4/1991 |
| EP | 0 435 518 A1 | 7/1991 |
| EP | 0 464 755 A1 | 1/1992 |
| EP | 0472731 | 3/1992 |
| EP | 0 472 731 A1 | 4/1992 |
| EP | 0 540 290 B1 | 5/1993 |
| EP | 0540290 | 5/1993 |
| EP | 0 551 179 A1 | 7/1993 |
| EP | 0 556 850 A1 | 8/1993 |
| EP | 0556850 | 8/1993 |
| EP | 0565251 | 10/1993 |
| EP | 0 565 251 A1 | 10/1993 |
| EP | 0 667 131 A2 | 1/1995 |
| EP | 0 689 806 A2 | 5/1995 |
| EP | 0686379 | 12/1995 |
| EP | 0 686 379 B1 | 12/1995 |
| EP | 0 696 447 A2 | 2/1996 |
| EP | 0 701 800 A1 | 3/1996 |
| EP | 0 705 577 A1 | 4/1996 |
| EP | 0 716 834 A1 | 6/1996 |
| EP | 0 747 020 A2 | 12/1996 |
| FR | 2 678 508 | 8/1993 |
| GB | 1 506 432 | 4/1978 |
| GB | 1506432 | 4/1978 |
| GB | 1567122 | 5/1980 |
| GB | 1 567 122 | 5/1980 |
| GB | 1 355 373 | 6/1994 |
| JP | 02-174859 | 7/1990 |
| JP | 06-007454 | 1/1994 |
| JP | 06-181993 | 7/1994 |
| JP | 7-500272 T | 1/1995 |
| JP | 07-024688 | 3/1995 |
| JP | 8-509899 T | 10/1996 |
| SU | 1635980 A1 | 12/1988 |
| WO | WO 88/06026 | 8/1988 |
| WO | WO 90/04982 | 5/1990 |
| WO | WO 92/03107 | 3/1992 |
| WO | WO 92/04097 | 3/1992 |
| WO | WO 92/06734 | 4/1992 |
| WO | WO 92/09246 | 6/1992 |
| WO | WO 93/13825 | 7/1993 |
| WO | WO 93/17636 | 9/1993 |
| WO | WO 93/19803 | 10/1993 |
| WO | WO 93/19804 | 10/1993 |
| WO | WO 93/22984 | 11/1993 |
| WO | WO 93/22986 | 11/1993 |
| WO | WO 93/22989 | 11/1993 |
| WO | WO 94/00179 | 1/1994 |
| WO | WO 94/01483 | 1/1994 |
| WO | WO 94/04097 | 3/1994 |
| WO | WO 94/12136 | 6/1994 |
| WO | WO 94/15549 | 7/1994 |
| WO | WO 95/01466 | 2/1995 |
| WO | WO 95/05131 | 2/1995 |
| WO | WO 95/05132 | 2/1995 |
| WO | WO 95/09586 | 4/1995 |
| WO | WO 95/21592 | 8/1995 |
| WO | WO 95/26695 | 10/1995 |
| WO | WO 96/10967 | 4/1996 |
| WO | WO 96/18360 | 6/1996 |
| WO | WO 96/18361 | 6/1996 |
| WO | WO 96/24306 | 8/1996 |
| WO | WO 97/21402 | 6/1997 |
| WO | WO 97/21403 | 6/1997 |
| WO | WO 97/21641 | 6/1997 |
| WO | WO 98/30173 | 7/1998 |

OTHER PUBLICATIONS

Blum, U. et al.; "Dacron Endografts for Infrarenal Abdominal Aortic Aneurysms: 2 Year Follow–Up"; Cardiovascular and Interventional Radiology. Springer, vol. 20, No. 1; Jan./Feb. 1997.

Chuter et al.; "Bifurcated stent–grafts for AAA: 3 year follow–up"; Abstracts from the Seventh International Course on Peripheral Vascular Intervention; J. Endovas. Surg. (1996) 3:453.

Chuter et al.; "Bifurcated stent–grafts for AAA: 3 year follow–up"; *Fifth International and Interdisciplinary Symposium on Endoluminal Stents and Grafts* (Oct. 10–13, 1996) Washington, D.C., 2 pages total.

Cragg et al., "Nitinol Intravascular Stent; Results of Preclinical Evaluation", Radiology 189(3): 775–778 (1993).

Cragg, "Percutaneous Femoropopliteal Graft Placement" Radiology 187(3): 643–648 (1993).

Cragg, et al.; "Percutaneous Femoropopliteal Graft Placement" Journal of Vascular and Interventional Radiology 4(4): 455–462 (1993).

Dereume, JP et al.; "Endoluminal Treatment Of Adbominal Aortic Aneurysm with the Corvita Endovascular Graft, Results of a Single–Center, Prospective Feasibility Study of 90 Patients"; *Abstracts from the Seventh International Course on Peripheral Vascular Intervention* J. Endovasc. Surg. (1996) 3:460–461.

Hagen et al., "Self–Expandable Macroporous Nitinol Stents for Transfemoral Exclusion of Aortic Aneurysm in Dogs" Cardiovascular Intervention Radiology 16:339–342 (1993).

Katzen et al., "initial experience performing combined surgical/interventional procedures in the interventional suite" *Abstracts from the Seventh International Course on Peripheral Vascular Intervention J. Endovasc. Surg.* (1996) 3:467.

Moore et al., "Transfemoral endovascular repair of abdominal aortic aneurysm: Result of the North American EVT phase 1 trail" J. Vasc. Surg. (1996) 23:543–552.

Parodi et al., "long–term follow–up of AAA endoluminal repair" *Abstracts from the Seventh International Course on Peripheral Vascular Intervention. J. Endovasc. Surg.* (1996) 3:335.

Product Brochure for Cook–ZTM Stents, Gianturco–Rosch Biliary Design, CookR, A Cook Groups Company, P.O. Box 489, Bloomington, IN, 47402, U.S.A., 4 pages total, (1989).

Product Brochure for Catheters, Guidewires, and Stents (no date) Schneider (USA) Inc., Pfizer Hospital Products Group, 5905 Nathan Lane, Minneapolis, Minnesota, 55442.

Product Brochure for Cook–ZTM Stents, Gianturco–Rosch Biliary Design, CookR, A Cook Groups Company, P.O. Box 489, Bloomington, IN, 47402, U.S.A., 4 pages total, (1989).

Product Brochure for PalmazTM Balloon–Expandable Stent, Johnson & Johnson Interventional Systems, 40 Technology Drive, P.O. Box 4917, Warren, NJ, 07059, 2 pages total, (1990).

White et al., "Endoleak following endoluminal repair of AAA: Diagnosis, significance, and amanagement" *Abstracts from the Seventh International Course on Peripheral Vascular Intervention J. Endovasc. Surg.* (1996) 3:339–340.

Wilson et al.; "A self expanding bifurcated endovascular graft for Abdominal Aortic Aneurysm Repair. An Initial Study in a Canine Model" ASAIO Journal 42(5): 386–393 (1996).

World Medical News, World Medical manufacturing Corporation, 13794 NW 4th Street, Bldgs. 210 & 211, Sunrise, Florida, 33325 U.S.A., vol. 5, Issue 3 (Jul. 1996) 3 pages total.

U.S. patent application Ser. No. 08/871,427 & pending claims as of Apr. 16, 2001, Filing date Jun. 6, 1997, Lau et al.

U.S. patent application Ser. No. 09/207,944 & response dated Aug. 21, 2000, Filing Date Dec. 9, 1998, Vonesh et al.

U.S. patent application Ser. No. 09/235,214, Jan. 22, 1999, Brauker et al.

U.S. patent application Ser. No. 09235,458 & response dated Sep. 28, 2000, Filing Date Jan. 22, 1999 Vonesh et al.

U.S. patent application Ser. No. 09/306,522, Filing Date May 6, 1999, Myers.

U.S. patent application Ser. No. 09/376,931 & pending claims as of Apr. 16, 2001, Filing Date Aug. 13, 1999, Martin, et al.

U.S. patent application Ser. No. 09/408,866 & response dated Jan. 10, 2001, Filing Date Sep. 30, 1999, Brenton et al.

U.S. patent application Ser. No. 09/488, 229, Filling Date Jan. 20, 2000, Cully et al.

U.S. patent application Ser. No. 09/489,604,Filing Date Jan. 20, 2000, Vonesh et al.

U.S. patent application Ser. No. 09/510,937 & response dated Oct. 5, 2000, Filing Date Feb. 22, 2000, Goffena et al.

Cragg, "Precutaneous femoropopliteal graft placement" *Radiology* (1993) 187(3):643–648.

Cragg et al., "Percutaneous femoropopliteal graft placement" *Journal of Vascular and Interventional Radiology* (1993) 4(4):433–462.

Cragg et al.,, "Nitinol intravascular stent: results of preclinical evaluation" *Radiology* (1993) 189:775–778.

Hagen et al., "Self–expandable macroporous nitinol stents for transfemoral exclusion of aortic aneurysms in dogs: preliminary results" *Cardiovasc. Intervent. Radiol.* (1993) 16:339–342.

Product Brochure for Cook–Z™ Stents, Gianturco–Rösch Biliary Design, Cook®, A Cook Groups Company, P.O. Box 489, Bloomington, IN, 47402, U.S.A., 4 pages total, (1989).

Product Brochure for Plamaz™ Balloon–Expandable Stent, Johnson & Johnson Interventional Systems, 40 Technology Drive, P.O. Box 4917, Warren, NJ, 07059, 2 pages total, (1990).

* cited by examiner

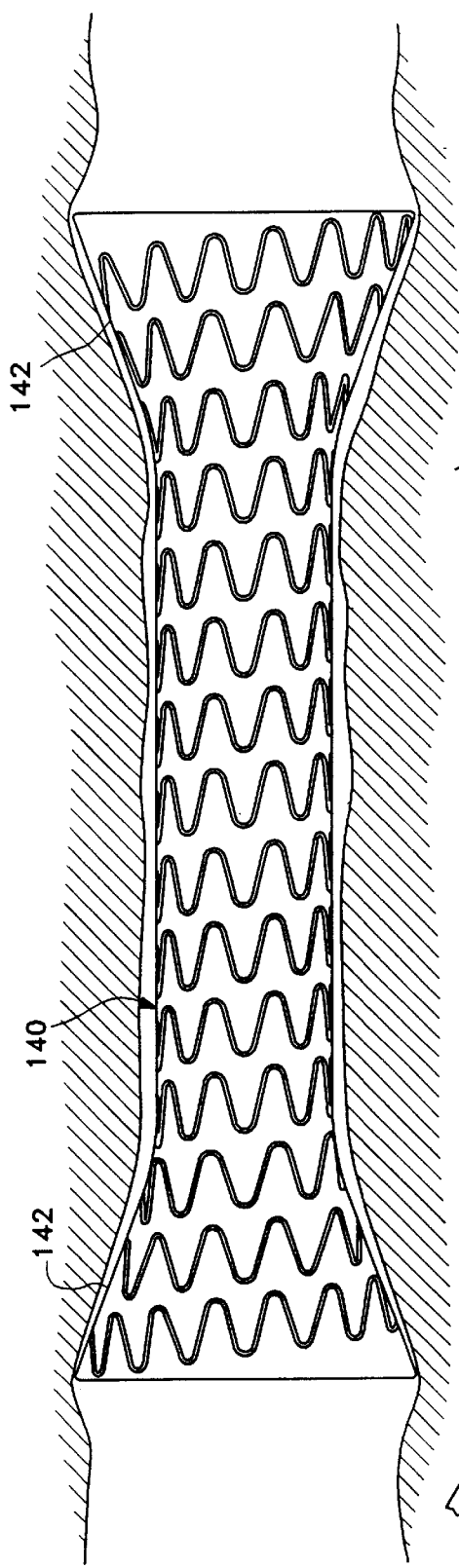
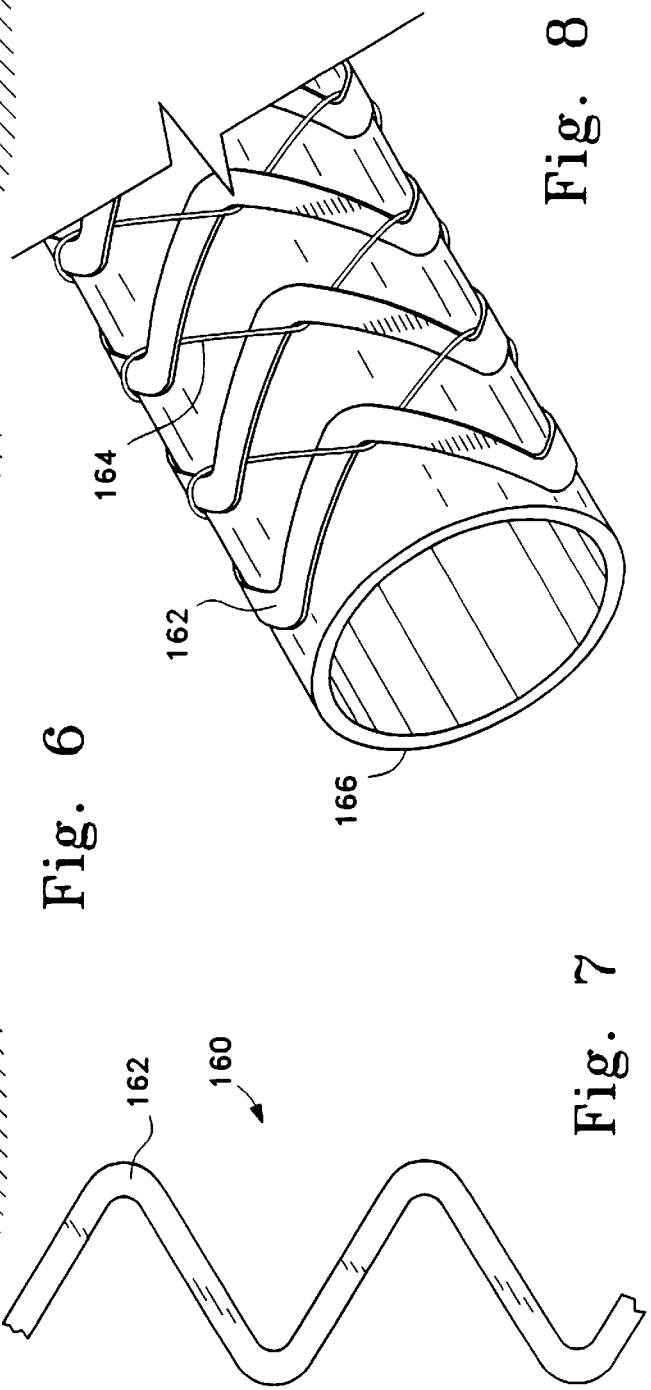
Fig. 6
Fig. 8
Fig. 7

EXTERIOR SUPPORTED SELF-EXPANDING STENT-GRAFT

This application is a continuation of 08/740,030 filed Oct. 23, 1996 now abandoned which is a continuation of 08/299,190 filed Aug. 31, 1994 now abandoned.

FIELD OF THE INVENTION

This invention is a medical device and a method of using it. The device is a foldable stent-graft which may be percutaneously delivered with (or on) an endovascular catheter or via surgical techniques or using other suitable techniques and then expanded. The stent-graft uses a kink-resistant stent structure and an interior graft which is attached to the stent in such a way that the graft does not kink and yet the stent is able to conform to curves in the blood vessel lumen.

The expandable stent structure preferably has a helically deployed torsional member with an undulating shape which is wound to form the generally cylindrical shape deployed as the stent. The helical winding desirably is aligned to allow the undulations in adjacent turns of the helix to be in phase. The adjacent undulating shapes may be held in that phased relationship using a flexible linkage, typically made of a polymeric material. The stent may also be of a ring configuration. The stent may be flared to promote smooth blood flow and to assure that the stent will remain in its chosen position.

The graft component cooperating with the stent is tubular and mounted on the interior of the stent. Although it may be made of any of a variety of materials, it preferably is an expanded polyfluorocarbon. The graft component may be attached to the stent in a variety of ways but desirably is bound to the flexible linkage which holds the stent windings in phase (or to the stent structure itself) at a number of sliding attachment points. This manner of attachment allows the stent to slide locally with respect to the graft structure or, in the case of the helically wound stent structure, allows the adjacent undulating shapes in adjacent helical turns to slide longitudinally with respect to each other as the stent is bent and still support the shape of the graft.

The stent-graft may be used to reinforce vascular irregularities, to provide a smooth nonthrombogenic interior vascular surface for diseased areas in blood vessels, or to increase blood flow past a diseased area of a vessel by mechanically improving the interior surface of the vessel. The inventive stent-graft is especially suitable for use within smaller vessels between 2 mm and 6 mm in diameter but is equally suitable for significantly larger vessels. The inventive stent-graft may be self-expandable; it is kink-resistant, easily bent along its longitudinal axis, and does not change its length during that expansion.

Included in the invention are methods for coupling the stent structure to the graft to optimize the flexibility and the kink resistance of the resulting stent-graft.

BACKGROUND OF THE INVENTION

Treatment or isolation of vascular aneurysms or of vessel walls which have been thinned or thickened by disease has traditionally been done via surgical bypassing with vascular grafts. Shortcomings of this procedure include the morbidity and mortality associated with surgery, long recovery times after surgery, and the high incidence of repeat intervention needed due to limitations of the graft or of the procedure. Vessels thickened by disease are currently sometimes treated less invasively with intraluminal stents that mechanically hold these vessels open either subsequent to or as an adjunct to a balloon angioplasty procedure. Shortcomings of current stents include the use of highly thrombogenic materials (stainless steels, tantalum, ELGILOY) which are exposed to blood, the general failure of these materials to attract and support functional endothelium, the irregular stent/vessel surface that causes unnatural blood flow patterns, and the mismatch of compliance and flexibility between the vessel and the stent.

Important to this invention is the use of less invasive intraluminal delivery and, in a preferred aspect, placement of a nonthrombogenic blood-carrying conduit having a smooth inner lumen.

The most desired variations of this invention involve a stent-graft which is self-expanding, which does not shorten upon delivery, which has excellent longitudinal flexibility, which has high radial compliance to the vessel lumen, and exposes the blood to a smooth, nonthrombogenic surface capable of supporting endothelium growth.

The inventive device may be delivered in a reduced diameter and expanded to maintain the patency of any conduit or lumen in the body. An area in which the inventive stent-graft is particularly beneficial is in the scaffolding of atherosclerotic lesions in the cardiovascular system to establish vessel patency, prevention of thrombosis, and the further prevention of restenosis after angioplasty. In contrast to many of the stents discussed below having metallic struts intruding into the blood flow in the vessel lumen which generate turbulence and create blood stasis points initiating thrombus formation, the smooth, continuous surface provided by the preferred tubular inner conduit of our invention provides a hemodynamically superior surface for blood flow.

Mechanically, the linked helical stent structure used in the stent-graft provides a good combination of radial strength and flexibility. The structure is also radially resilient. It can be completely crushed or flattened and yet spring open again once the obstructive loading is removed. This ability is important for use in exposed portions of the body around the peripheral vasculature or around joints. The stent-graft can sustain a crushing traumatic blow or compression from the bending of a joint and still return to the open configuration once the load is removed.

With regard to delivery, the self-expansion mechanism eliminates the need for a balloon catheter and the associated balloon rupture problems often associated with that delivery procedure. In addition, the absence of the bulk of the balloon allows a smaller delivery profile to be achieved. Unlike some other self-expanding stent designs, this stent-graft maintains a constant length throughout the expansion process. Thus, the stent-graft does not have some of the positioning problems associated with other many self-expanding stents. In treating longer lesions, our self-expanding design eliminates the need for special long balloons or repositioning of the balloon between inflations in order to expand the entire length of the stent.

The impermeability of the preferred stent-graft makes it suitable for shunting and thereby hydraulically isolating aneurysms. The expansile properties derived from the stent structure provide a secure anchor to the vessel wall.

Stents

The stents currently described in the open literature include a wide variety of different shapes.

Wallsten, U.S. Pat. No. 4,655,771, suggests a vascular prosthesis for transluminal implantation which is made up of a flexible tubular body having a diameter that is varied by adjusting the axial separation of the two ends of the body relative to each other. In general, the body appears to be a woven device produced of various plastics or stainless steel.

U.S. Pat. No. 4,760,849, to Kroph, shows the use of a ladder-shaped coil spring which additionally may be used as a filter in certain situations.

Porter, U.S. Pat. No. 5,064,435, suggests a stent made up of two or more tubular stent segments which may be deployed together so to produce a single axial length by a provision of overlapping areas. This concept is to permit the use of segments of known length, which, when deployed, may be used together in overlapping fashion additively to provide a stent of significant length.

Quan-Gett, U.S. Pat. No. 5,151,105, discloses an implantable, collapsible tubular sleeve apparently of an outer band and an inner spring used to maintain the sleeve in a deployed condition.

Wall, U.S. Pat. No. 5,192,307, suggests a stent having a number of holes therein and which is expandable using an angioplasty balloon so to allow ratchet devices or ledges to hold the stent in an open position once it is deployed.

Perhaps of more relevance are the patents using wire as the stent material.

Gianturco, in U.S. Pat. Nos. 4,580,568 and 5,035,706, describes stents formed of stainless steel wire arranged in a closed zigzag pattern. The stents are compressible to a reduced diameter for insertion into and removal from a body passageway. The stents appear to be introduced into the selected sites by discharge of the collapsed zigzag wire configuration from the tip of a catheter.

U.S. Pat. Nos. 4,830,003 and 5,104,404, to Wolff et al., shows a stent of a zigzag wire configuration very similar in overall impression to the Gianturco device. However, the stent is said to be self-expanding and therefore does not need the angioplasty balloon for its expansion.

Hillstead, U.S. Pat. 4,856,516, suggests a stent for reinforcing vessel walls made from a single elongated wire. The stent produced is cylindrical and is made up of a series of rings which are, in turn, linked together by half-hitch junctions produced from the single elongated wire.

Wiktor, U.S. Pat. Nos. 4,649,992, 4,886,062, 4,969,458, and 5,133,732, shows wire stent designs using variously a zigzag design or, in the case of Wiktor '458, a helix which winds back upon itself. Wiktor '062 suggests use of a wire component made of a low-memory metal such as copper, titanium or gold. These stents are to be implanted using a balloon and expanded radially for plastic deformation of the metal.

Wiktor '458 is similarly made of low-memory alloy and is to be plastically deformed upon its expansion on an angioplasty balloon.

Wiktor '732 teaches the use of a longitudinal wire welded to each turn of the helically wound zig-zag wire which is said to prevent the longitudinal expansion of the stent during deployment. A further variation of the described stent includes a hook in each turn of the helix which loops over a turn in an adjacent turn.

WO93/13825, to Maeda et al, shows a self-expanding stent similar to the Gianturco, Wolff, and Wiktor designs, formed of stainless steel wire, which is built into an elongated zig-zag pattern, and helically wound about a central axis to form a tubular shape interconnected with a filament. The bends of the helix each have small loops or "eyes" at their apexes which are interconnected with a filament. Because of the teaching to connect the eyes of the apexes, the stent appears to be a design that axially expands during compression and may tear attached grafts because of the relative change in position of the arms of the zig-zag during compression of the stent.

MacGregor, U.S. Pat. No. 5,015,253, shows a tubular non-woven stent made up of a pair of helical members which appear to be wound using opposite "handedness". The stent helices desirably are joined or secured at the various points where they cross.

Pinchuk, in U.S. Pat. Nos. 5,019,090, 5,092,877, and 5,163,958, suggests a spring stent which appears to circumferentially and helically wind about as it is finally deployed except, perhaps, at the very end link of the stent. The Pinchuk '958 patent further suggests the use of a pyrolytic carbon layer on the surface of the stent to present a porous surface of improved antithrombogenic properties.

U.S. Pat. No. 5,123,917, to Lee, suggests an expandable vascular graft having a flexible cylindrical inner tubing and a number of "scaffold members" which are expandable, ring-like, and provide circumferential rigidity to the graft. The scaffold members are deployed by deforming them beyond their plastic limit using, e.g., an angioplasty balloon.

Tower, in U.S. Pat. Nos. 5,161,547 and 5,217,483, shows a stent formed from a zig-zag wire wound around a mandrel in a cylindrical fashion. It is said to be made from "a soft platinum wire which has been fully annealed to remove as much spring memory as possible." A longitudinal wire is welded along the helically wound sections much in the same way as was the device of Wiktor.

There are a variety of disclosures in which super-elastic alloys such as nitinol are used in stents. See, U.S. Pat. No. 4,503,569, to Dotter; U.S. Pat. No. 4,512,338, to Balko et al.; U.S. Pat. No. 4,990,155, to Wilkoff; U.S. Pat. No. 5,037,427, Harada, et al.; U.S. Pat. No. 5,147,370, to MacNamara et al.; U.S. Pat. No. 5,211,658, to Clouse; and U.S. Pat. No. 5,221,261, to Termin et al. None of these references suggest a device having discrete, individual, energy-storing torsional members as are required by this invention.

Jervis, in U.S. Pat. Nos. 4,665,906 and 5,067,957, describes the use of shape memory alloys having stress-induced martensite properties in medical devices which are implantable or, at least, introduced into the human body.

Stent-Grafts

A variety of stent-graft designs are shown in the following literature.

Perhaps the most widely known such device is shown in Ersek, U.S. Pat. No. 3,657,744. Ersek shows a system for deploying expandable, plastically deformable stents of metal mesh having an attached graft through the use of an expansion tool.

Palmaz describes a variety of expandable intraluminal vascular grafts in a sequence of patents: U.S. Patent Nos. 4,733,665; 4,739,762; 4,776,337; and 5,102,417. The Palmaz '665 patent suggests grafts (which also function as stents) that are expanded using angioplasty balloons. The grafts are variously a wire mesh tube or of a plurality of thin bars fixedly secured to each other. The devices are installed, e.g., using an angioplasty balloon and consequently are not seen to be self-expanding.

The Palmaz '762 and '337 patents appear to suggest the use of thin-walled, biologically inert materials on the outer periphery of the earlier-described stents.

Finally, the Palmaz '417 patent describes the use of multiple stent sections each flexibly connected to its neighbor.

Rhodes, U.S. Pat. No. 5,122,154, shows an expandable stent-graft made to be expanded using a balloon catheter. The stent is a sequence of ring-like members formed of links spaced apart along the graft. The graft is a sleeve of a material such as expanded a polyfluorocarbon, e.g., GORE-TEX or IMPRAGRAFT.

Schatz, U.S. Pat. No. 5,195,984, shows an expandable intraluminal stent and graft related in concept to the Palmaz patents discussed above. Schatz discusses, in addition, the use of flexibly-connecting vascular grafts which contain several of the Palmaz stent rings to allow flexibility of the overall structure in following curving body lumen.

Cragg, "Percutaneous Femoropopliteal Graft Placement", *Radiology,* vol. 187, no. 3, pp. 643–648 (1993), shows a stent-graft of a self-expanding, nitinol, zig-zag, helically wound stent having a section of polytetrafluoroethylene tubing sewed to the interior of the stent.

Cragg (European Patent Application 0,556,850) discloses an intraluminal stent made up of a continuous helix of zig-zag wire and having loops at each apex of the zig-zags. Those loops on the adjacent apexes are individually tied together to form diamond-shaped openings among the wires. The stent may be made of a metal such as nitinol (col. 3, lines 15–25 and col. 4, lines 42+) and may be associated with a "polytetrafluoroethylene (PTFE), dacron, or any other suitable biocompatible material". Those biocompatible materials may be inside the stent (col. 3, lines 52+) or outside the stent (col. 4, lines 6+). There is no suggestion that the zig-zag wire helix be re-aligned to be "in phase" rather than tied in an apex-to-apex alignment. The alignment of the wire and the way in which it is tied mandates that it expand in length as it is expanded from its compressed form.

Grafts

As was noted above, the use of grafts in alleviating a variety of vascular conditions is well known. Included in such known grafting designs and procedures are the following.

Medell, U.S. Pat. No. 3,479,670, discloses a tubular prothesis adapted to be placed permanently in the human body. It is made of framework or support of a synthetic fiber such as DACRON or TEFLON. The tube is said to be made more resistant to collapse by fusing a helix of a polypropylene monofilament to its exterior. The reinforced fabric tube is then coated with a layer of collagen or gelatin to render the tubing (to be used as an esophageal graft) impermeable to bacteria or fluids.

Sparks, in U.S. Pat. Nos. 3,514,791, 3,625,198, 3,710,777, 3,866,247, and 3,866,609, teach procedures for the production of various graft structures using dies of suitable shape and a cloth reinforcing material within the die. The die and reinforcement are used to grow a graft structure using a patient's own tissues. The die is implanted within the human body for a period of time to allow the graft to be produced. The graft is in harvested and implanted in another site in the patient's body by a second surgical procedure.

Braun, in U.S. Pat. No. 3,562,820, shows a biological prosthesis manufactured by applying onto a support of a biological tissue (such as serosa taken from cattle intestine) a collagen fiber paste. The procedure is repeated using multiple layers of biological tissue and collagen fiber paste until a multi-layer structure of the desired wall thicknesses is produced. The prosthesis is then dried and removed prior to use.

Dardik et al, U.S. Pat. No. 3,974,526, shows a procedure for producing tubular prostheses for use in vascular reconstructive surgeries. The prosthesis is made from the umbilical cord of a newly born infant. It is washed with a solution of 1 percent hydrogen peroxide and rinsed with Ringer's lactate solution. It is then immersed in a hyaluronidase solution to dissolve the hyaluronic acid coating found in the umbilical cord. The vessels are then separated from the cord and their natural interior valving removed by use of a tapered mandrel. The vessels are then tanned with glutaraldehyde. A polyester mesh support is applied to the graft for added support and strength.

Whalen, U.S. Pat. No. 4,130,904, shows a prosthetic blood conduit having two concentrically associated tubes with a helical spring between them. Curved sections in the tube walls help prevent kinking of the tube.

Ketharanathan, U.S. Pat. No. 4,319,363, shows a procedure for producing a vascular prosthesis suitable for use as a surgical graft. The prosthesis is produced by implanting a rod or tube in a living host and allowing collagenous tissue to grow on the rod or tube in the form of coherent tubular wall. The collagenous implant is removed from the rod or tube and tanned in glutaraldehyde. The prosthesis is then ready for use.

Bell, U.S. Pat. No. 4,546,500, teaches a method for making a vessel prosthesis by incorporating a contractile agent such as smooth muscle cells or platelets into a collagen lattice and contracting the lattice around a inner core. After the structure has set, additional layers are applied in a similar fashion. A plastic mesh sleeve is desirably sandwiched between the layers or imbedded within the structure to provide some measure of elasticity.

Hoffman Jr. et al, U.S. Pat. No. 4,842,575, shows a collagen impregnated synthetic vascular graft. It is made of a synthetic graft substrate and a cross-linked collagen fibril. It is formed by depositing a aqueous slurry of collagen fibrils into the lumen of the graft and massaging the slurry into the pore structure of the substrate to assure intimate admixture in the interior. Repeated applications and massaging and drying is said further to reduce the porosity of the graft.

Alonoso, U.S. Pat. No. 5,037,377, is similar in overall content to the Hoffman Jr. et al patent discussed above except that, in addition to collagen fibers, soluble collagen is introduced into the fabric. A suitable cross-linking agent such as glutaraldehyde is used to bond adjacent collagen fibers to each other.

Slepian et al, U.S. Pat. No. 5,213,580, teaches a process described as "paving" or "stabilizing by sealing the interior surface of a body vessel or organ" by applying a biodegradable polymer such as a polycaprolactone. The polymer is made into a tubular substrate, placed in position, and patched into place.

Finally, there are known vascular grafts using collagenous tissue with reinforcing structure. For instance, Pinchuk, in U.S. Pat. Nos. 4,629,458 and 4,798,606, suggests the use of collagen with some other type of fibrous structure supporting the collagen as a biograft. Similarly, Sinofsky et al., U.S. Pat. No. 5,100,429, suggests a partially-cured, collagen-based material used to form a graft within a blood vessel.

Kreamer, U.S. Pat. No. 4,740,207, suggests a intraluminal graft made of a semi-rigid resilient tube, open along a seam extending from one end to the other, which is expanded within the vessel and which resulting larger diameter is maintained by use of a ledge at the longitudinal seam for catching the opposite side of the seam on the expanded graft.

The use of expanded polyfluorocarbons in vascular devices is shown in British patent Nos. 1,506,432, and 1,567,122, which patents show in particular blood vessel linings of the material.

None of the cited references suggest a stent-graft similar to that described herein.

SUMMARY OF THE INVENTION

This invention is a foldable stent-graft which may be percutaneously delivered through or over a catheter, typically an endovascular catheter, or using surgical techniques or other appropriate methodologies.

The incorporated expandable stent structure utilizes torsional regions which allow it to be folded to a very small diameter prior to deployment. Preferably, the torsional members have an undulating shape which may be helically wound to form the stent's cylindrical shape. The undulating shape may be aligned to allow the undulations in adjacent turns of the helix to be in phase. Adjacent undulating shapes may be held in the phased relationship using a flexible linkage, often made of a polymeric material. In the helically wound variation of the invention, the undulating torsional members do not have any means at (or near) the apex of the undulating shapes which would tend to constrict the movement of the flexible linkage during compression or bending of the stent. The stent is preferably made of a highly flexible, superelastic alloy such as nitinol, but may be of any suitable elastic material such as various of the medically accepted stainless steels. The stent structure may also be of a series of rings incorporating the torsional members which rings may be axially linked.

The graft component used to complement the stent is typically tubular, placed within the stent, and may be made of a polymeric material which may be attached variously to the filament used to maintain the shape of the stent structure, when such filament is used, or to the stent structure itself. Preferably, the graft component is a biocompatible, expanded polyfluoroethylene polymer. The attachment between the graft component and the stent, e.g., by bonding the graft component to the flexible linkage or by using eyelets or other discrete or continuous linking sites, is carefully crafted to allow the stent torsional members to slide longitudinally with respect to each other and to the graft component and so maintain the interior shape of graft. This is to say that the graft component is supported at a variety of sites located along its outer surface. Bending the stent-graft combination distributes the flexing movement of the graft over a long region because of the distributed support of the stent. The tendency of the graft component to kink in a single site is minimized and the resultant flexing is observed to take place in a collection of smaller non-kinking bends located among the tie points to the stent or the stent's filament.

The stent-graft may be used to reinforce vascular irregularities and provide a smooth interior vascular surface, particularly within smaller vessels.

BRIEF DESCRIPTION OF THE DRAWINGS

FIG. 6 is a side view of the inventive stent-graft showing a variation having flared ends.

FIG. 7 shows a plan view of an unrolled stent produced from flat stock.

FIG. 8 shows a front quarter view of the rolled stent using the flat stock pattern shown in FIG. 7.

DESCRIPTION OF THE INVENTION

Figure 1A:
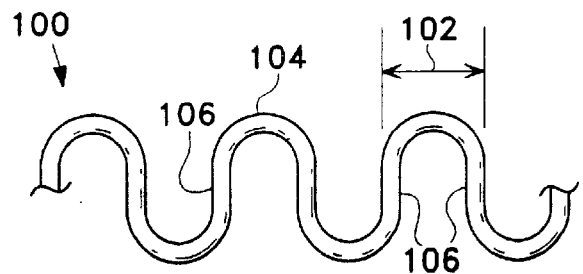
FIGS. 1A, 1B, 1C, 1D, and 1E are plan views of an unrolled stent form suitable for use in the invention.

As was noted above, this invention is an expandable stent-graft and a method of using it. The stent-graft is a combination of several components: first, a thin-walled tube forming the graft component which graft component is generally coaxial to and within the stent and, second, the expandable stent structure. The graft material may optionally contain a fibrous reinforcement material. The expandable stent structure is a cylindrical body produced either of a helically placed (wound or otherwise preformed) torsion member having an undulating or serpentine shape or a series of axially situated rings comprising those torsion members. When the undulating torsion member is formed into the cylinder, the undulations may be aligned so that they are "in phase" with each other. The helically wound undulations are desirably linked, typically with a flexible linkage of a suitable polymeric or metallic material, to maintain the phased relationship of the undulations during compression and deployment and during bending of the stent. These stent configurations are exceptionally kink-resistant and flexible, particularly when flexed along the longitudinal axis of the stent.

Central to the invention is the distributed attachment of the stent component to the graft component via, e.g., the bonding of the graft to the filament which may used to maintain the stent in its tubular shape or via bonding to other loops, eyelets, or fasteners associated with or adhering to the stent component.

The stent-graft may be delivered percutaneously, typically through the vasculature, after having been folded to a reduced diameter. Once reaching the intended delivery site, it is expanded to form a lining on the vessel wall.

Stent Component

Our stent is constructed of a reasonably high strength material, i.e., one which is resistant to plastic deformation when stressed. The structure is typically from one of three sources:

1.) a wire form in which a wire is first formed into an undulating shape and the resulting undulating shape is helically wound to form a cylinder, 2.) an appropriate shape formed from a flat stock and wound into a cylinder, and 3.) a length of tubing formed into an appropriate shape.

These stent structures are typically oriented coaxially with the tubular graft component. The stent structures are, at least, placed on the outer surface of the graft although, in certain configurations, an additional graft structure may be placed on the outer surface of the stent. When the outer graft structure is utilized, the stent structure should have the strength and flexibility to tack the graft tubing firmly and conformally against the vessel wall. In order to minimize the wall thickness of the stent-graft, the stent material should have a high strength-to-volume ratio. Use of designs as depicted herein provides stents which may be shorter in length than those often used in the prior art. Additionally, the designs do not suffer from a tendency to twist (or helically unwind) or to shorten as the stent-graft is deployed. As will be discussed below, materials suitable in these stents and meeting these criteria include various metals and some polymers.

A percutaneously delivered stent-graft must expand from a reduced diameter, necessary for delivery, to a larger deployed diameter. The diameters of these devices obviously vary with the size of the body lumen into which they are placed. For instance, the stents of this invention may range in size (for neurological applications) from 2.0 mm in diameter to 30 mm in diameter (for placement in the aorta). A range of about 2.0 mm to 6.5 mm (perhaps to 10.0 mm) is believed to be desirable. Typically, expansion ratios of 2:1 or more are required. These stents are capable of expansion ratios of up to 5:1 for larger diameter stents. Typical expansion ratios for use with the stents-grafts of the invention typically are in the range of about 2:1 to about 4:1 although the invention is not so limited. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thicknesses of about 0.002 inches to 0.005 inches is usually sufficient. For the larger stents, the appropriate thickness for the stent flat stock may be somewhat thicker, e.g., 0.005 to 0.020 inches.

The stent-graft is fabricated in the expanded configuration. In order to reduce its diameter for delivery the stent-graft would be folded along its length, similar to the way in which a PCTA balloon would be folded. It is desirable, when using super-elastic alloys which are also have temperature-memory characteristics, to reduce the diameter of the stent at a temperature below the transition-temperature of the alloys. Often the phase of the alloy at the lower temperature is somewhat more workable and easily formed. The temperature of deployment is desirably above the transition temperature to allow use of the super-elastic properties of the alloy.

As a generic explanation of the mechanical theory of a stent suitable for use in this invention, reference is made to FIGS. 1A, 1B, 1C, 1D, 1E, 2, 3, and 4.

FIG. 1A is a plan view of an isolated section of the stent which may be used in the stent-graft of the invention. The Figure is intended both to identify a variation of the invention and to provide conventions for naming the components of the torsion member (100). FIG. 1A shows, in plan view, an undulating torsion member (100) formed from a wire stock into a U-shape. A torsion pair (102) is made up of an end member (104) and two adjacent torsion lengths (106). Typically, then, each torsion length (106) will be a component to each of its adjacent torsion pairs (102). The U-shaped torsion pair (102) may be characterized by the fact that the adjacent torsion lengths are generally parallel to each other prior to formation into the stent.

Generically speaking, the stents of this invention use undulating torsion members which are "open" or "unconfined" at their apex or end member (104). By "open" or "unconfined" we mean that the apex or end member (104) does not have any means in that apex which would tend to inhibit the movement of the flexible linkage (discussed below) down between the arms or torsion lengths (106) of the torsion pair (102).

Figure 1B:
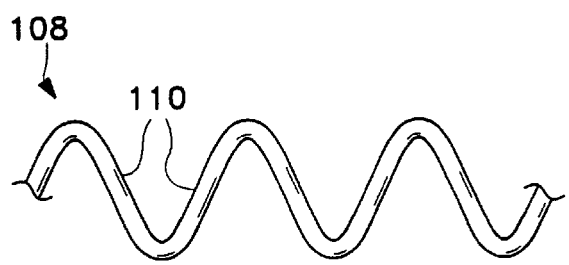

FIG. 1B shows another variation of the stent having a sinusoidal shaped torsion member (108). In this variation, the adjacent torsion lengths (110) are not parallel and the wire forms an approximate sinusoidal shape before being formed into a cylinder.

Figure 1C:
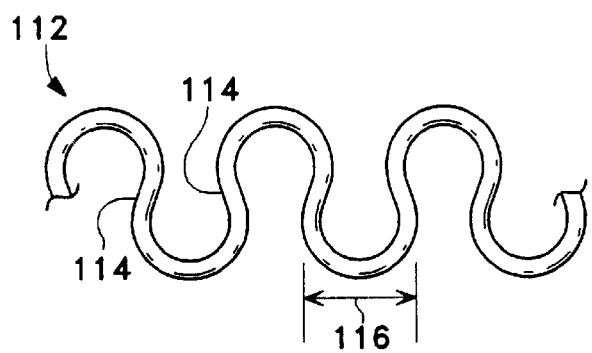

FIG. 1C shows a variation of the stent having an ovoid shaped torsion member (112). In this variation, the adjacent torsion lengths (114) are again not parallel. The wire forms an approximate open-ended oval with each torsion pair (116) before being formed into a cylinder.

Figure 1D:
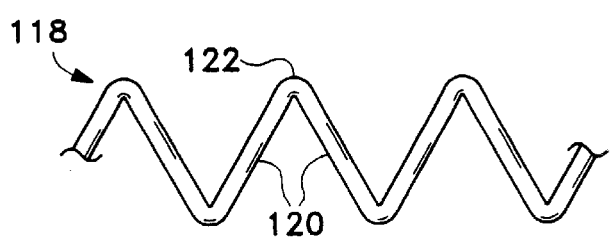

FIG. 1D shows another variation of the stent having a V-shaped torsion member (118). In this variation, the adjacent torsion lengths (120) form a relatively sharp angle at the torsion end (999) shape before being formed into a cylinder.

Figure 1E:
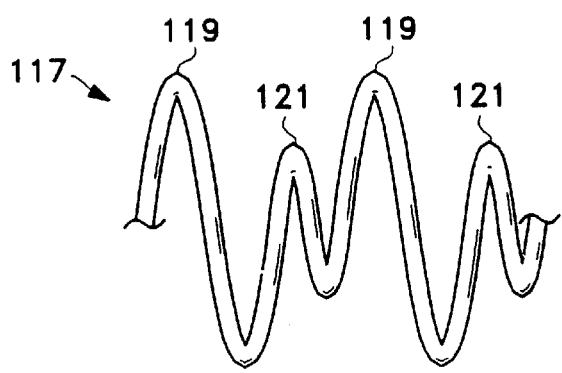

FIG. 1E shows a variation in which adjacent torsion members on the stent (117) have differing amplitude. The peaks of the high amplitude torsion members (119) may be lined up "out of phase" or "peak to peak" with short amplitude (121) or high amplitude torsion members in the adjacent turn of the helix or may be positioned "in phase" similar to those discussed with regard to FIG. 2 below.

The configurations shown in FIGS 1A–1E are exceptionally kink-resistant and flexible when flexed along the longitudinal axis of the stent.

As ultimately deployed, a section of the torsion member found on one of FIGS. 1A–1D would be helically wound about a form of an appropriate size so that the end members (e.g., 104 in FIG. 1A) would be centered between the end members of the torsion member on an adjacent turn of the helix. This is said to be "in phase". "Out of phase" would be the instance in which the adjacent members meet directly, i.e., end member-to-end member. In any event, once so aligned, the phasic relationship may be stabilized by weaving a flexible linkage through the end members from one turn of the helix to the next.

Figure 2:
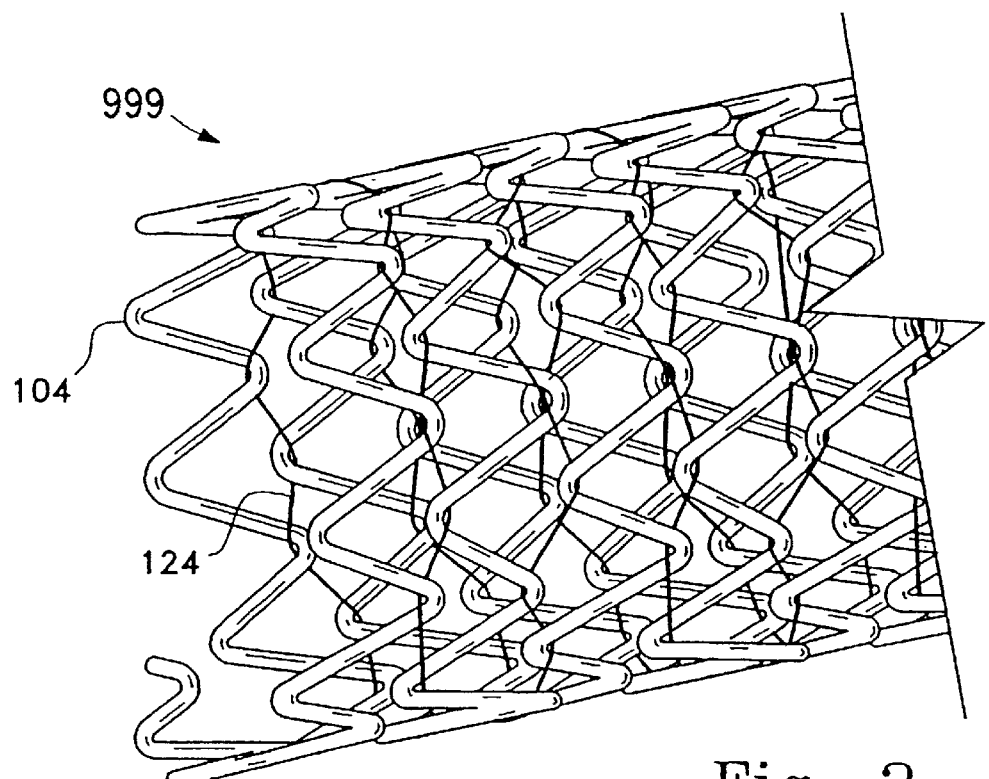
FIG. 2 is a side view of a stent suitable for use in this invention.

FIG. 2 shows a side view of one typical stent (999) made according to this invention including the phased relationship of the helical turns of the stent and the flexible linkage (124).

Figure 3:
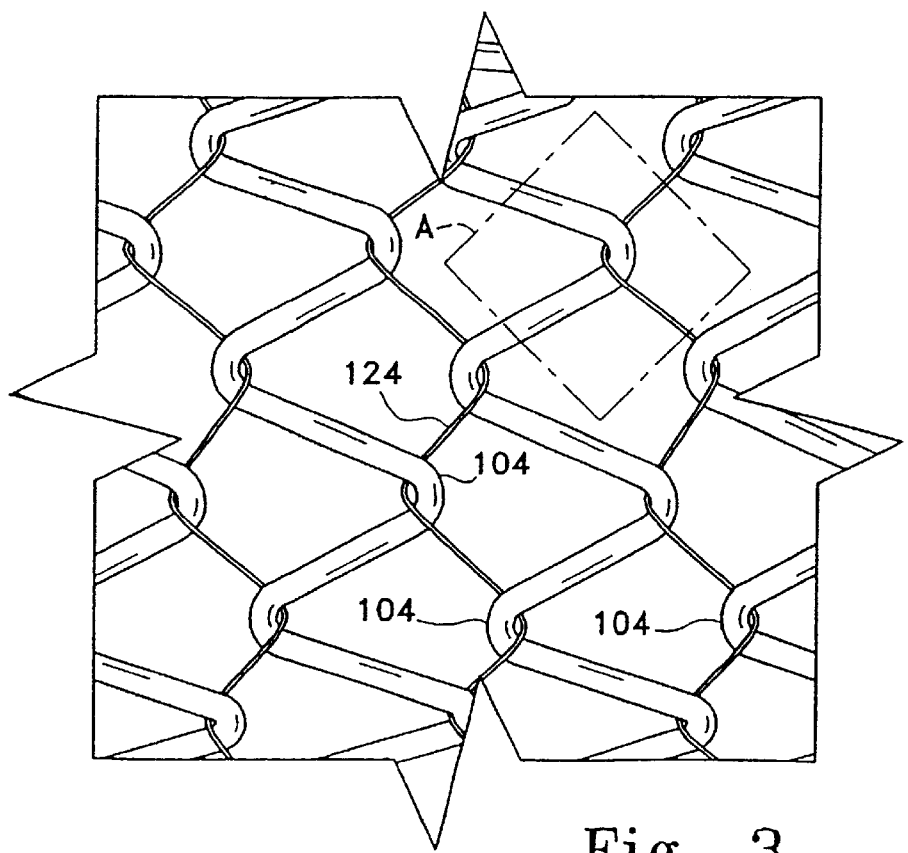
FIG. 3 is a close-up of a portion of the stent shown in FIG. 2.

FIG. 3 shows a close-up of the FIG. 2 stent and depicts the phased relationship (within box A) and shows in detail a typical way in which the flexible linkage (124) is looped through the various end members (104) to maintain the phased relationship. It may be noted that the flexible linkage (124) is free to move away from the apex at the end members (104) without constraint.

Figure 4:
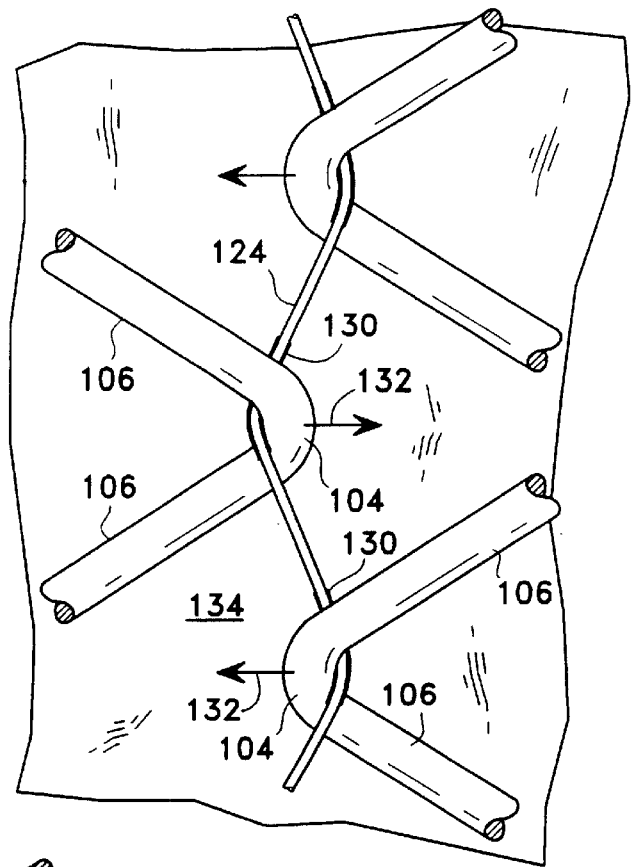
FIGS. 4 and 5 show magnified portions of the inventive stent-graft depicting methods of attaching the stent to the graft component.

FIG. 4 shows a magnified portion of a stent-graft (viewed from the outside of the stent-graft) incorporating a stent such as is shown in FIGS. 2 and 3 and depicts a method for distributively attaching the stent to the graft component. Specifically, end member or apex (104) is flanked by side lengths (106) and is looped therethrough by a filament (124). The graft component (134) is seen in the background. The filament (124) adheres to the graft (134) at the locations of contact (130) between the filament (124) and the graft component (134). It should be apparent that the apexes (104) are free to move in the direction shown by arrows (132) when the stent-graft is flexed. This shows the ability of the various apexes to move longitudinally with respect to each other and yet retain the graft component (134) reasonably snug against the inner surface of the stent and thereby prevent kinking of that graft component (134).

Figure 5:
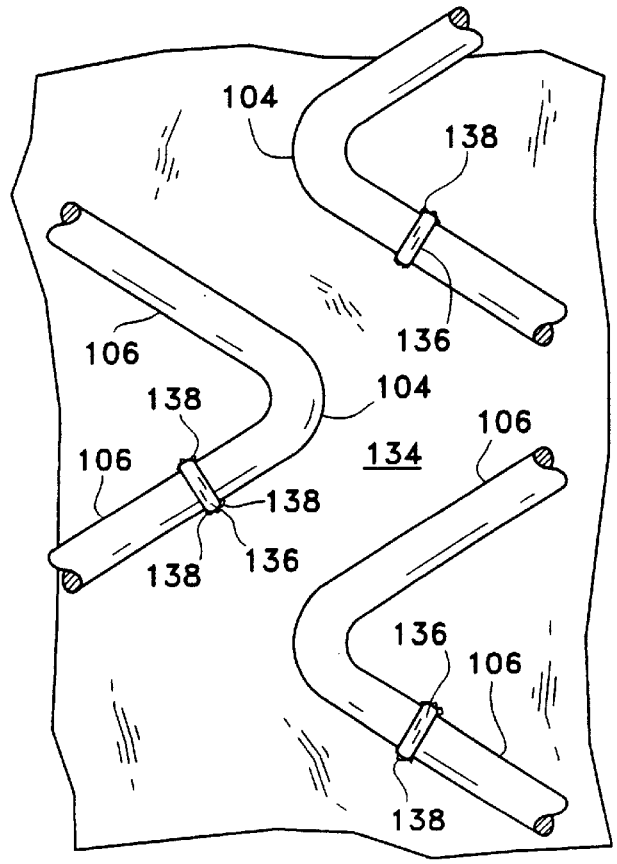

FIG. 5 shows a close-up of a section of a stent-graft according to the invention that is similar to the stent-graft portion shown in FIG. 4 but in which the stent is attached to the graft using loops (136) or eyelets on the stent. Again this shows a manner of distributively attaching the stent to the graft component (134). Again, end member or apex (104) is flanked by side lengths (106). Although no filament (124 in FIG. 4) is shown in the variation in FIG. 5, it is contemplated that the filament (124) may be used in conjunction with loops (136). The graft component (134) is seen in the background. These loops (136) may be of a material which adheres to the graft component (134) at the junctions shown at (138). It is also contemplated that the filament (124) may be of material which is either adherent to (such as a melt-miscible thermoplastic polymer) or not adherent to (such as a metal or thermoset polymer) the graft component (134) when used with the loops (136).

The scope of materials for the filament (124), graft component (134), and loops (136) will be discussed in detail below.

FIG. 6 shows, in side view, a variation of the stent (140) support structure made from wire and having flares (142) at one or both ends. The flaring provides a secure anchoring of the resulting stent-graft (140) against the vessel wall and prevents the implant from migrating downstream. In addition, the flaring provides a tight seal against the vessel so that the blood is channelled through the lumen rather than outside the graft. The undulating structure may vary in spacing to allow the helix turns to maintain their phased relationship between turns of the helix and to conform to the discussion just above. A flexible linkage between the contiguous helical turns is not shown but may also be applied to at least a portion of the helices.

The stent support structure may also be made by forming a desired structural pattern out of a flat sheet. The sheet may then be rolled to form a tube. FIG. 7 shows a plan view of torsion members (160) which may be then rolled about an axis to form a cylinder. As is shown in FIG. 8, the end caps (162) may be aligned so that they are "in phase". The flexible linkage (164) may then be included to preserve the diameter of the stent. The graft component (166) is shown on the inner surface of the stent. Loops may be used as was described above. The graft may be attached to the loops or filament in the manner discussed above.

The stent shown in FIG. 8 may be machined from tubing. If the chosen material in nitinol, careful control of temperature during the machining step may be had by EDM (electro-discharge-machining), laser cutting, chemical machining, or high pressure water cutting.

Figure 9:
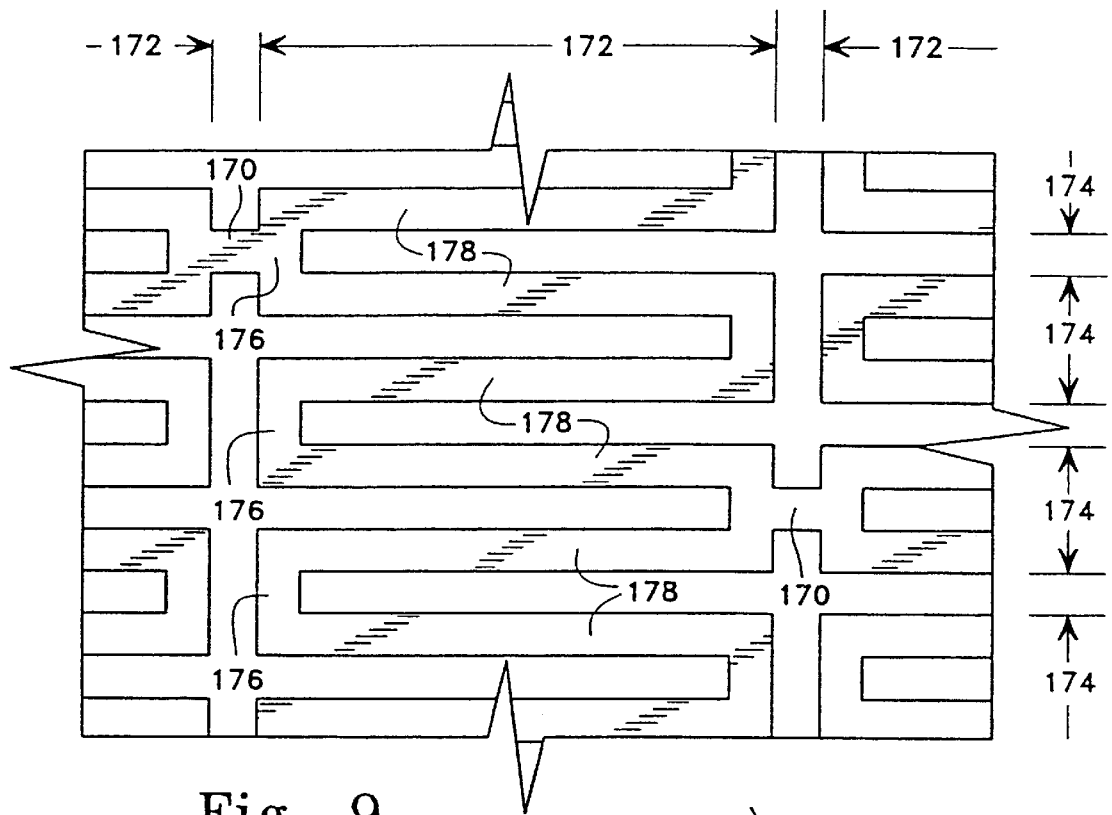
FIG. 9 shows a plan view of an unrolled stent produced from flat stock having a ringed structure.

FIG. 9 is a conceptual schematic of an isolated ring section of another variation of the stent component useful in this invention. The FIG. 9 is intended only to identify and to provide conventions for naming the components of the ring. FIG. 9 shows, in plan view, of the layout of the various components of a ring as if they were either to be cut from a flat sheet and later rolled into tubular formation for use as a stent with welding or other suitable joining procedures taking place at the seam or (if constructed from tubing) the layout as if the tubing was cut open. The portion of the stent between tie members (170) is designated as a ring (172) or ring section. Tie members (170) serve to link one ring (172) to an adjacent ring (172). A torsion pair (174) is made up of a cap member (176) and two adjacent torsion members (178). Typically, then, each torsion member (178) will be a component to each of its adjacent torsion pairs (174).

Figure 10:
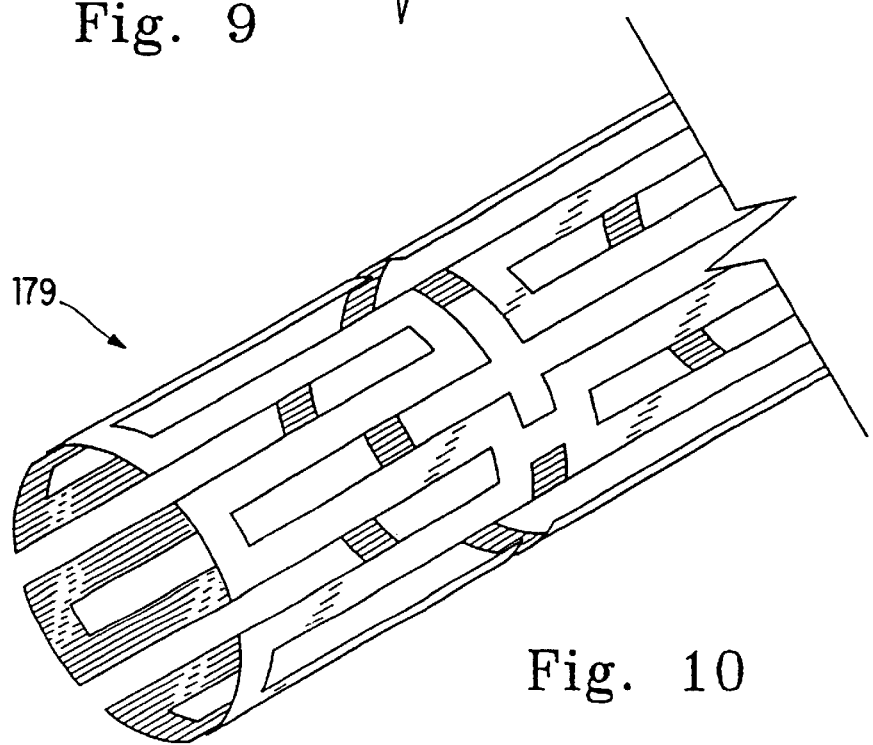
FIG. 10 shows a front quarter view of the rolled ring structured stent using the flat stock pattern shown in FIG. 9.

As ultimately deployed, a roll of the sheet found in FIG. 9 would be entered into the body lumen. Typically, it would be folded in some fashion which will be discussed below. A front quarter perspective view of the rolled stent (179) is shown in the FIG. 10.

Figure 11:
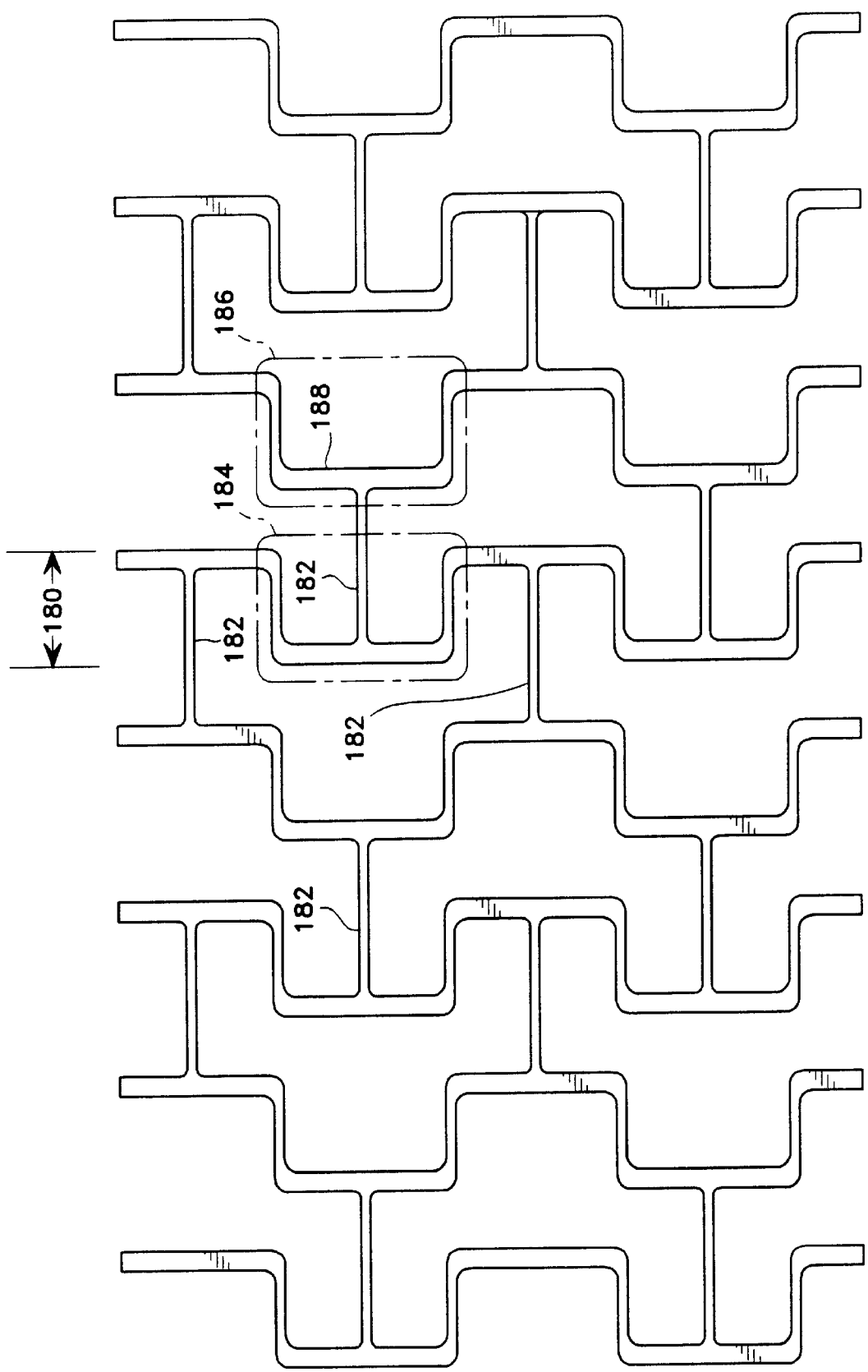
FIGS. 11, 12, and 13 show plan views of variations of unrolled stents made according to the invention.

FIG. 11 shows a variation of the stent having a ring section (180) similar in configuration to that shown above and joined by tie members (182). Those tie members (182) extend from the inside of a torsion pair (184) to the outside of a torsion pair (186) in the adjacent ring section. The tie members (182) experience no twisting because of their placement in the middle of end cap (188). The tie members may be offset on the end cap, if so desired, to allow the tie members to accept some of the twisting duty.

Figure 12:
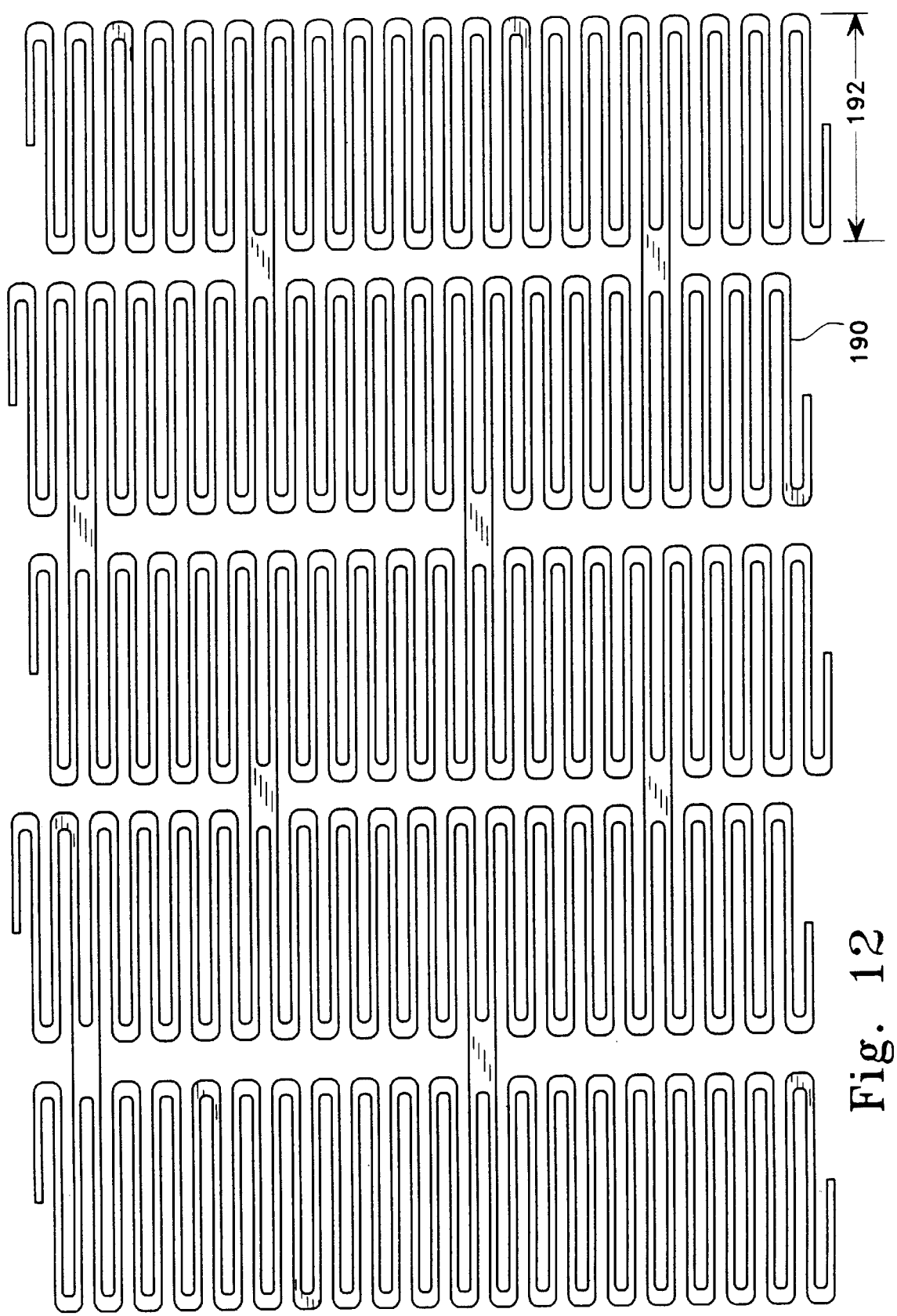

FIG. 12 shows a plan view of a variation of the inventive stent in which the number of torsion members (190) in a selected ring member (192) is fairly high. This added number of torsion members may be due to a variety of reasons. For instance, the material of construction may have a significantly lower tolerance for twisting than the materials in those prior Figures. Adding more torsion bars lessens the load carried on each of the several bars. Alternatively, for the same material, the stent may need to be folded to a smaller diameter for deployment than those earlier variations.

Figure 13:
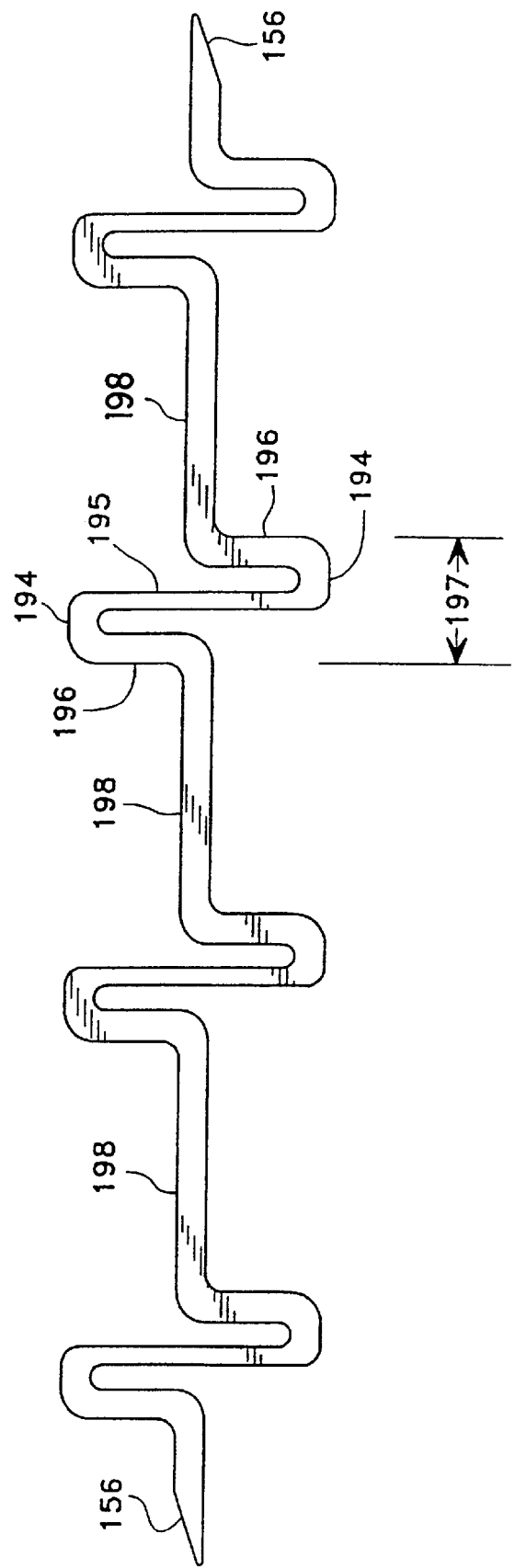

FIG. 13 shows a variation of the invention (156) in which the end caps (194) are bound by a long torsion member (195) and two short torsion members (196). This torsion set (197) is in turn separated from the adjacent torsion set (197) by a bridge member (198) which shares the bending load of the stent when the stent is rolled and the ends (199) joined by, e.g., welding. The short torsion members (196) have a greater width than that of the long torsion member (195) so to balance the load around the ring during deformation and thereby to prevent the bridge members from becoming askew and out of the ring plane.

It should be clear that a variety of materials variously metallic, super elastic alloys, and preferably nitinol, are suitable for use in these stents. Primary requirements of the materials are that they be suitably springy even when fashioned into very thin sheets or small diameter wires. Various stainless steels which have been physically, chemically, and otherwise treated to produce high springiness are suitable as are other metal alloys such as cobalt chrome alloys (e.g., ELGILOY), platinum/tungsten alloys, and especially the nickel-titanium alloys generically known as "nitinol".

Nitinol is especially preferred because of its "super-elastic" or "pseudo-elastic" shape recovery properties, i.e., the ability to withstand a significant amount of bending and flexing and yet return to its original form without deformation. These metals are characterized by their ability to be transformed from an austenitic crystal structure to a stress-induced martensitic structure at certain temperatures, and to return elastically to the austenitic shape when the stress is released. These alternating crystalline structures provide the alloy with its super-elastic properties. These alloys are well known but are described in U.S. Pat. Nos. 3,174,851, 3,351,463, and 3,753,700. Typically, nitinol will be nominally 50.6% (±0.2%) Ni with the remainder Ti. Commercially available nitinol materials usually will be sequentially mixed, cast, formed, and separately cold-worked to 30–40%, annealed, and stretched. Nominal ultimate yield strength values for commercial nitinol are in the range of 30 psi and for Young's modulus are about 700 Kbar.

The '700 patent describes an alloy containing a higher iron content and consequently has a higher modulus than the Ni-Ti alloys.

Nitinol is further suitable because it has a relatively high strength to volume ratio. This allows the torsion members to be shorter than for less elastic metals. The flexibility of the stent-graft is largely dictated by the length of the torsion member components in the stent structural component. The shorter the pitch of the device, the more flexible the stent-graft structure can be made. Materials other than nitinol are suitable. Spring tempered stainless steels and cobalt-chromium alloys such as ELGILOY are also suitable as are a wide variety of other known "super-elastic" alloys.

Although nitinol is preferred in this service because of its physical properties and its significant history in implantable medical devices, we also consider it also to be useful in a stent because of its overall suitability with magnetic resonance imaging (MRI) technology. Many other alloys, particularly those based on iron, are an anathema to the practice of MRI causing exceptionally poor images in the region of the alloy implant. Nitinol does not cause such problems.

Other materials suitable as the stent include certain polymeric materials, particularly engineering plastics such as thermotropic liquid crystal polymers ("LCP's"). These polymers are high molecular weight materials which can exist in a so-called "liquid crystalline state" where the material has some of the properties of a liquid (in that it can flow) but retains the long range molecular order of a crystal. The term "thermotropic" refers to the class of LCP's which are formed by temperature adjustment. LCP's may be prepared from monomers such as p,p'-dihydroxy-polynucleararomatics or dicarboxy-polynuclear-aromatics. The LCP's are easily formed and retain the necessary interpolymer attraction at room temperature to act as high strength plastic artifacts as are needed as a foldable stent. They are particularly suitable when augmented or filled with fibers such as those of the metals or alloys discussed below. It is to be noted that the fibers need not be linear but may have some preforming such as corrugations which add to the physical torsion enhancing abilities of the composite.

The flexible linkage between adjacent turns of the helix (124 in FIGS. 2, 3, 4, and 8) or the loops (136 in FIG. 5) may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), much preferred in this invention is the use of polymeric biocompatible filaments. Synthetic polymers such as polyethylene, polypropylene, polyurethane, polyglycolic acid, polyesters, polyamides, their mixtures, blends, copolymers, mixtures, blends and copolymers are suitable; preferred of this class are polyesters such as polyethylene terephthalate including DACRON and MYLAR and polyaramids such as KEVLAR, polyfluorocarbons such as polytetrafluoroethylene with and without copolymerized hexafluoropropylene (TEFLON or GORETEX), and porous or nonporous polyurethanes. Natural materials or materials based on natural sources such as collagen may also be used is this service.

As will be discussed below, the material chosen for the linkage or the loops is preferably of a material which can be bonded to the graft liner in a distributed sequence of points along the outside surface of the graft liner. By bonding the liner to the linkage or the loops in such fashion, the flexibility and resistance to kinking of the stent is maintained in the resulting stent-graft. To state the central concept of the invention in another way, the graft component is to be distributively attached to the stent structure at a number of sites. The attachments should allow some movement between the graft component and the stent at the attachment points. This may be accomplished by causing adherence of the graft independently to at least some of the linkage, to the loops, or to one or the other. Other structural attachments may be used to meet the functional requirements recited here.

Tubular Component Materials

The tubular component or graft member of the stent-graft may be made up of any material which is suitable for use as a graft in the chosen body lumen. Many graft materials are known, particularly known are those used as vascular graft materials. For instance, natural materials such as collagen may be introduced onto the inner surface of the stent and fastened into place. Desirable collagen-based materials include those described in U.S. Pat. No. 5,162,430, to Rhee et al, and WO 94/01483 (PCT/US93/06292), the entirety of which are incorporated by reference. Synthetic polymers such as polyethylene, polypropylene, polyurethane, polyglycolic acid, polyesters, polyamides, their mixtures, blends, copolymers, mixtures, blends and copolymers are suitable; preferred of this class are polyesters such as polyethylene terephthalate including DACRON and MYLAR and polyaramids such as KEVLAR, polyfluorocarbons such as polytetrafluoroethylene with and without copolymerized hexafluoropropylene (TEFLON or GORETEX), and porous or nonporous polyurethanes. Especially preferred in this invention are the expanded fluorocarbon polymers (especially PTFE) materials described in British. Pat. Nos. 1,355,373, 1,506,432, or 1,506,432 or in U.S. Pat. No. 3,953,566, U.S. Pat. No. 4,187,390, or U.S. Pat. No. 5,276,276, the entirety of which are incorporated by reference.

Included in the class of preferred expanded fluoropolymers are polytetrafluoroethylene (PTFE), fluorinated ethylene propylene (FEP), copolymers of tetrafluoroethylene (TFE) and per fluoro(propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is expanded PTFE.

In addition, one or more radio-opaque metallic fibers, such as gold, platinum, platinum-tungsten, palladium, platinum-iridium, rhodium, tantalum, or alloys or composites of these metals like may be incorporated into the device, particularly, into the graft, to allow fluoroscopic visualization of the device.

The tubular component may also be reinforced using a network of small diameter fibers. The fibers may be random, braided, knitted, or woven. The fibers may be imbedded in the tubular component, may be placed in a separate layer coaxial with the tubular component, or may be used in a combination of the two.

Production of the Stent-Graft

The preferred method of constructing the stent-graft is to first construct the stent incorporating a filamentary linkage of the type discussed above and then to place the tubular component inside the stent. The tubular component is then expanded using a mandrel or the like and heated to allow the materials of the filamentary linkage and the tubular graft component to merge and self-bind.

Loops may be molded into or glued onto the graft component and later attached to the stent or linkage or the loops may be independently introduced and tied onto the stent structure.

Deployment of the Invention

When a stent-graft having torsion members is folded, crushed, or otherwise collapsed, mechanical energy is stored in torsion in those torsion members. In this loaded state, the torsion members have a torque exerted about them and consequently have a tendency to untwist. Collectively, the torque exerted by the torsion members as folded down to a reduced diameter must be restrained from springing open. The stent typically has at least one torsion member per fold to take advantage of the invention. The stent-graft is folded along its longitudinal axis and restrained from springing open. The stent-graft is then deployed by removing the restraining mechanism, thus allowing the torsion members to spring open against the vessel wall.

The attending physician will choose a stent or stent-graft having an appropriate diameter. However, inventive devices of this type are typically selected having an expanded diameter of up to about 10% greater than the diameter of the lumen to be the site of the stent deployment.

The stent-graft may be tracked through the vasculature to the intended deployment site and then unfolded against the vessel lumen. The graft tube component of the stent-graft is flexible and easy to fold. Folding or otherwise collapsing the stent structure allows it to return to a circular, open configuration.

Figure 14A:
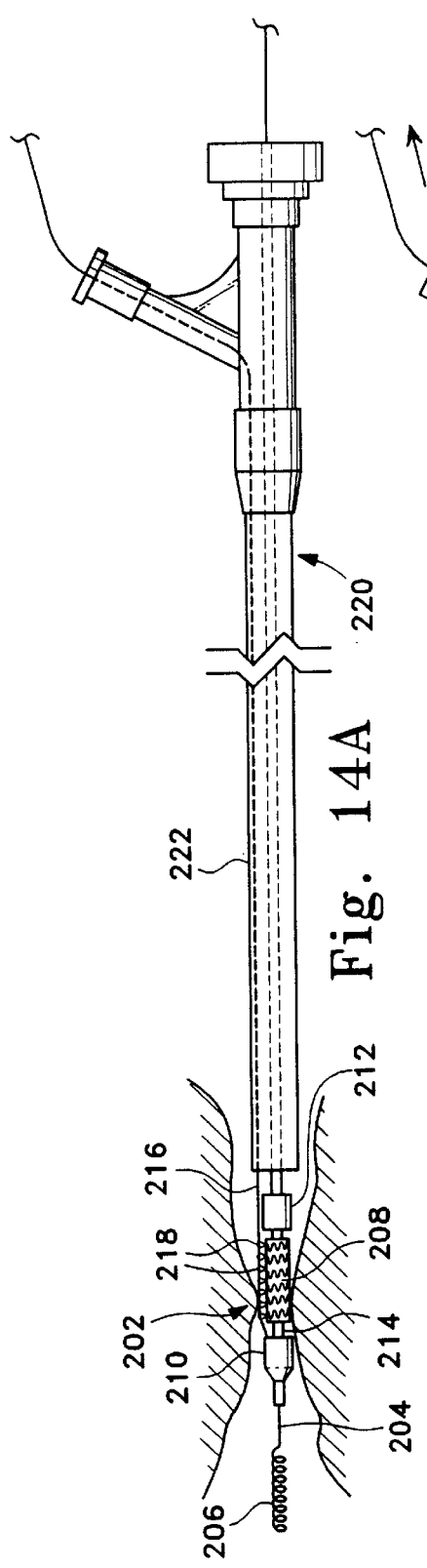
FIGS. 14A–14C show a schematic procedure for deploying the inventive stent-grafts.
Figure 14B:
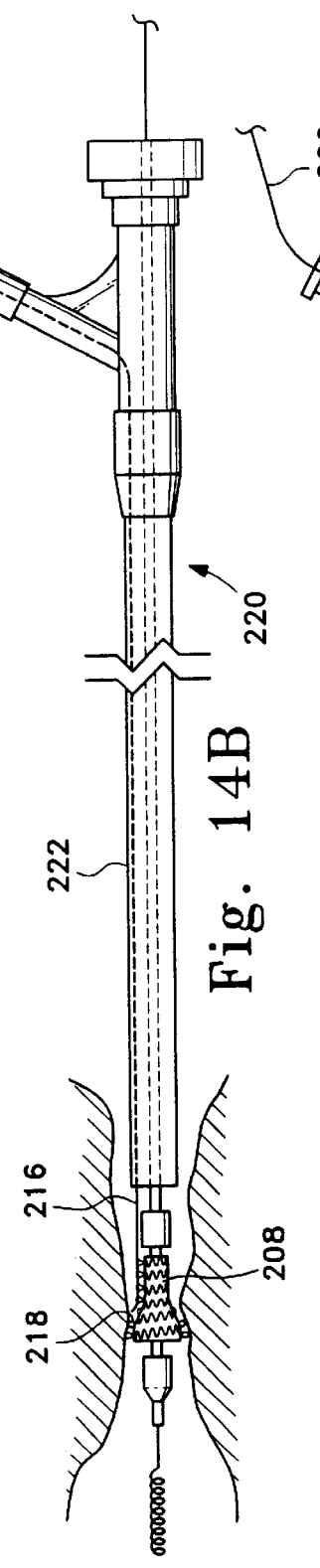
Figure 14C:
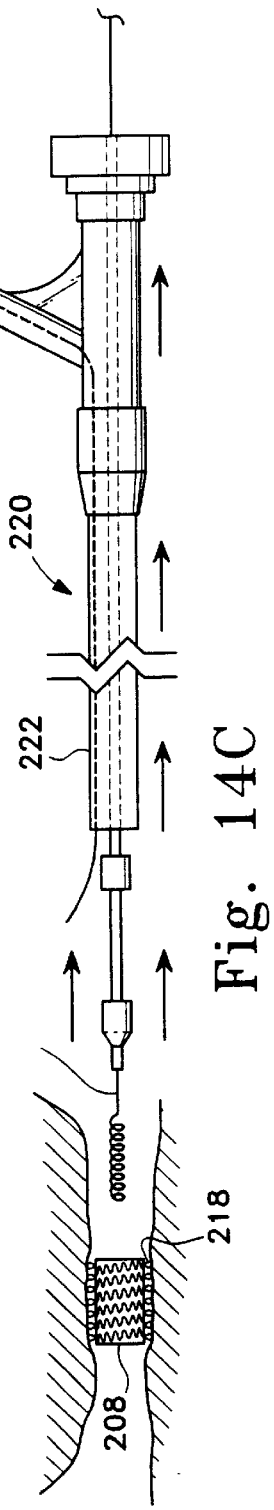

FIGS. 14A–14C show a method for deployment of the devices of the present invention and allow them to self-expand. FIG. 11A shows a target site (202) having, e.g., a narrowed vessel lumen. A guidewire (204) having a guide tip (206) has been directed to the site using known techniques. The stent-graft (208) is mounted on guidewire (204) and is held in place prior to deployment by distal barrier (210) and proximal barrier (212). The distal barrier (210) and proximal barrier (212) typically are affixed to the guidewire tube (214). The tether wire (216) is shown extending through loops (218) proximally through the catheter assembly's (220) outer jacket (222) through to outside the body.

FIG. 14B shows the removal of the tether wire (216) from a portion of the loops (218) to partially expand the stent-graft (208) onto the selected site (202).

FIG. 14C shows the final removal of the tether wire (216) from the loops (218) and the retraction of the catheter assembly (220) from the interior of the stent-graft (208). The stent-graft (208) is shown as fully expanded.

Other methods of deployment are suitable for use with this device and are described in U.S. patent application Ser. Nos. 07/927,165 and 07/965,973, the entirety of which are incorporated by reference.

Many alterations and modifications may be made by those of ordinary skill in the art without departing from the spirit and scope of the invention. The illustrated embodiments have been shown only for purposes of clarity and examples, and should not be taken as limiting the invention as defined by the following claims, which include all equivalents, whether now or later devised.

We claim as our invention:

1. A device comprising:
   a support component having multiple turns of an undulating member, said member being formed from a single continuous wire, each turn of said undulating member having multiple undulations defining multiple apexes, with undulations in one turn generally in-phase with undulations in an adjacent turn; and
   a tubular graft component substantially coaxial with said support component, said tubular graft component being attached to said support component only in-part, allowing unattached apexes to move longitudinally relative to said graft component; and
   said support component being slidably secured to said graft component such that relative movement therebetween is limited.

2. A device comprising:
   a support component comprising multiple turns of an undulating member, said member being formed from a single continuous wire, each turn of said undulating member having multiple undulations which define multiple apexes, wherein undulations in one turn are generally in-phase with undulations in an adjacent turn; and
   a tubular graft component positioned substantially coaxially within said support component, said tubular graft component being attached to said support component to allow said apexes to move longitudinally relative to said graft component.

3. The device of claim 2 wherein said member is a helical member configured to form said support component and which forms said multiple turns of said support component.

4. The device of claim 3 further comprising at least one flexible link, said flexible link coupling adjacent helical turns of said support component to maintain said undulations generally in-phase.

5. The device of claim 4, wherein said flexible link is secured to said graft component at least in-part.

6. The device of claim 2 further comprising at least one loop passing around at least a portion of one of said undulations to attach said support component to said graft component.

7. The device of claim 2 wherein the support component comprises wire and the undulations have a sinusoidal shape.

8. The device of claim 2 wherein the support component comprises wire and the undulations are U-shaped.

9. The device of claim 2 wherein the support component comprises wire and the undulations are V-shaped.

10. The device of claim 2 wherein the support component comprises wire and the undulations are ovaloid shaped.

11. The device of claim 2 wherein the support component comprises a stainless steel material or a titanium alloy.

12. The device of claim 2 wherein the support component comprises a nickeltitanium alloy.

13. The device of claim 2 wherein the tubular graft component comprises polyethylene terephthalate.

14. The device of claim 2 wherein the tubular graft component comprises polytetrafluoroethylene.

15. The device of claim 14 wherein the polytetrafluoroethylene is expanded.

16. The device of claim 14 wherein the polytetrafluoroethylene includes hexafluoropropylene.

17. The device of claim 2 wherein the tubular graft comprises a polyfluorocarbon.

18. The device of claim 2 further comprising radiopaque markers within said tubular graft member.

19. A stent-graft comprising:
   a self expanding stent comprising an undulating member, said member being formed from a single continuous wire arranged in a helical configuration with multiple turns and having multiple undulations, each undulation having an apex, undulations in adjacent turns being generally in-phase with one another; and
   a graft positioned substantially coaxially within said stent, said graft being attached to said stent to allow said apexes to move longitudinally relative to said graft.

20. The device of claim 19 further comprising at least one flexible link, said flexible link coupling adjacent helical turns of said support component to maintain said undulations generally in-phase.

21. The device of claim 19 wherein the stent comprises a stainless steel material or a titanium alloy.

22. The device of claim 19 wherein the stent comprises a stainless steel material or a titanium alloy.

23. The device of claim 19 wherein the graft comprises a polyfluorocarbon.

* * * * *